US009611457B2

(12) United States Patent
Mihovilovic et al.

(10) Patent No.: US 9,611,457 B2
(45) Date of Patent: Apr. 4, 2017

(54) TRIAZINE DERIVATIVES AS DIFFERENTIATION CATALYSTS

(71) Applicants: Marko Mihovilovic, Perchtoldsdorf (AT); Michael Schnuerch, Steinbrunn Neue Siedlung (AT); Karlheinz Hilber, Vienna (AT); Xaver Koenig, Moedling (AT); Thomas Linder, Vienna (AT); Agnes Mike, Vienna (AT)

(72) Inventors: Marko Mihovilovic, Perchtoldsdorf (AT); Michael Schnuerch, Steinbrunn Neue Siedlung (AT); Karlheinz Hilber, Vienna (AT); Xaver Koenig, Moedling (AT); Thomas Linder, Vienna (AT); Agnes Mike, Vienna (AT)

(73) Assignee: TECHNISCHE UNIVERSITAET WIEN, Vienna (AT)

( * ) Notice: Subject to any disclaimer, the term of this patent is extended or adjusted under 35 U.S.C. 154(b) by 153 days.

(21) Appl. No.: 14/346,328

(22) PCT Filed: Sep. 21, 2012

(86) PCT No.: PCT/AT2012/050140
§ 371 (c)(1),
(2) Date: Mar. 21, 2014

(87) PCT Pub. No.: WO2013/040622
PCT Pub. Date: Mar. 28, 2013

(65) Prior Publication Data
US 2014/0234965 A1    Aug. 21, 2014

(30) Foreign Application Priority Data
Sep. 21, 2011  (AT) .................. A 1364/2011

(51) Int. Cl.
*C12N 5/071*   (2010.01)
*C12N 5/077*   (2010.01)
*C07D 251/44*  (2006.01)
*C07D 251/46*  (2006.01)
*C07D 251/48*  (2006.01)
*C07D 251/50*  (2006.01)

(52) U.S. Cl.
CPC ......... *C12N 5/0657* (2013.01); *C07D 251/44* (2013.01); *C07D 251/46* (2013.01); *C07D 251/48* (2013.01); *C07D 251/50* (2013.01); *C12N 2501/999* (2013.01); *C12N 2506/30* (2013.01)

(58) Field of Classification Search
None
See application file for complete search history.

(56) References Cited

U.S. PATENT DOCUMENTS

| 2011/0136681 A1 | 6/2011  | Preynat-Seauve et al. |
| 2012/0294835 A1 | 11/2012 | Mihovilovic et al.    |
| 2013/0142860 A1 | 6/2013  | Kruse et al.          |

FOREIGN PATENT DOCUMENTS

| AT | 509266 A1        | 7/2011  |            |
| DE | 102007034679 A1  | 1/2009  |            |
| DE | WO 2009012901 A2 * | 1/2009 | ............ A61K 35/55 |
| WO | WO 2002079197 A1 | 10/2002 |            |
| WO | WO 2006000420 A1 | 1/2006  |            |
| WO | WO 2010144423 A1 | 12/2010 |            |
| WO | WO 2011079343 A2 | 7/2011  |            |
| WO | WO 2011088031 A1 | 7/2011  |            |

OTHER PUBLICATIONS

Lewandowski et al. "Techniques for the induction of human pluripotent stem cell differentiation towards cardiomyocytes", Journal of Tissue Engineering and Regenerative Medicine, published online 2016.*
Yamakawa et al. "Strategies for heart regeneration: approaches ranging from induced pluripotent stem cells to direct cardiac reprograming", International Heart Journal 56(1): 1-5, 2015.*
Schwach et al. "Generation and purification human stem cell-derived cardiomyocytes", Differentiation, 2016 in press.*
Sachidanandan, et al., "Identification of a Novel Retiniod by Small Molecule Screening with Zebrafish Embryos", PLOS ONE, Bd. 3, Nr. 4, Jan. 1, 2008, p. 1947.
Donna, et al., "A New Insight into the Histogenesis of Mesodermomas malignant Mesotheliomas", Histopathology (Oxford), Bd. 19, Nr. 3, Apr. 8, 1991, pp. 239-244.
Ding Sheng, et al., "A Role for Chemistry in Stem Cell Biology", Nature Biotechnology, vol. 22, Nr. 7, Jul. 2004 Nature Publishing Group, New York.

* cited by examiner

*Primary Examiner* — Emily Cordas
(74) *Attorney, Agent, or Firm* — Leydig, Voit & Mayer, Ltd.

(57) ABSTRACT

A method of inducing differentiation of mammalian cells into cardiomyocyte-like cells by contacting the mammalian cell with a triazine compound of formula (I), wherein X is independently —$NR_4$— or —O—, $R_4$ is hydrogen or $C_{1-6}$-alkyl; $R_1$ is hydroxy, $C_{1-6}$-alkyl, $C_{1-6}$-alkoxy, carboxy, $C_{1-6}$-alkoxycarbonyl, halo, cyano, nitro, formyl, amino, $C_{1-6}$-alkylamino, or di-$C_{1-6}$-alkylamino, the $C_{1-6}$-alkyl or -alkoxy residue being optionally substituted with one or more $R_5$ substituents selected from hydroxy, halo, cyano, and nitro; n is 0 to 5; $R_2$ is hydrogen, aryl, heteroaryl, or $C_{1-6}$-alkyl, the aryl or heteroaryl residue being optionally substituted with one or more $R_1$ substituents, and where the $C_{1-6}$-alkyl is optionally further substituted with one or more $R_5$ substituents; and $R_3$ is selected from hydrogen, halo, $NR_4R_7$, $OR_7$, $SR_7$, and $R_7$, where the same options apply for $R_7$ as for $R_2$; with the proviso that the compound of formula (I) is not 3-[(4,6-diphenoxy-1,3,5-triazin-2-yl)amino]benzoic acid.

20 Claims, No Drawings

TRIAZINE DERIVATIVES AS DIFFERENTIATION CATALYSTS

CROSS-REFERENCE TO RELATED APPLICATIONS

The present application is the national stage of international application PCT/AT2012/050140, filed on Sept. 21, 2012, and claims the benefit of the filing date of Austrian application No. A 1364/2011, filed on Sept. 21, 2011.

The invention relates to the use of certain triazine derivatives for inducing the differentiation of mammalian cells into cardiac muscle cells.

In general, Cell differentiation is a process in which a less specialized cell is converted into a more specialized cell type. However, cell differentiation is not only essential for the development of a fetus but also a common process with adults, for example, as stem cells divide and form completely differentiated daughter cells, e.g. in the repair of damaged tissue. Induction of the differentiation of cells is influenced by various factors which often bind to receptors on the cell surface.

It has been attempted for a while to influence the differentiation of certain cells, for example, to specifically induce it or to control its course. For example, it has been found that compounds of the cardiogenol series promote the differentiation of stem cells into cardiac muscle cells, which is of particular interest as the heart is one of the few organs to have hardly any regenerative abilities.

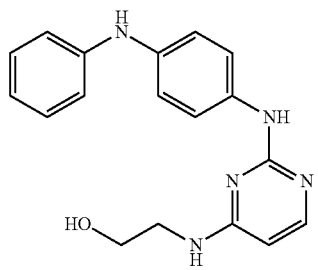

Cardiogenol A

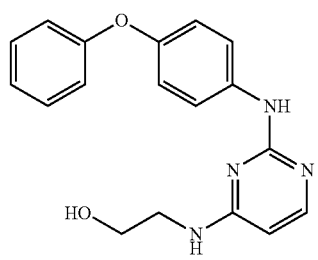

Cardiogenol B

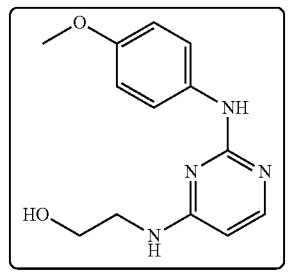

Cardiogenol C

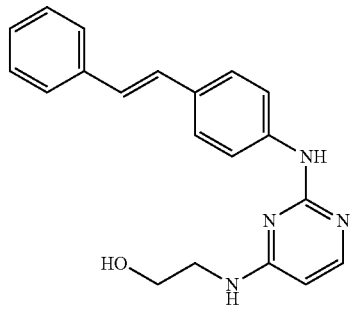

Cardiogenol D

By means of such pyrimidine derivatives, for example, (stem) cell therapies following cardiac infarctions could be improved.

In WO 2006/000420 A1, Novartis discloses compounds in which two of X, Y and Z are each N and the third is N or C—$R_5$, and which comprise an extremely wide range of options for the substituents $R_1$ to $R_5$, if present (with $R_5$ not even being defined in more detail in the main claim):

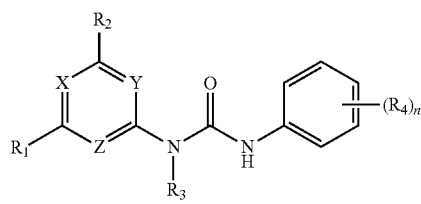

Such pyrimidine- or triazine-urea derivatives should be effective as kinase inhibitors.

The present inventors also have synthesized amino-substituted pyrimidine and pyridine derivatives in their previous patent application AT 509.266 A1, in which X represents either N oder CH, $R_3$ and $R_4$ may be hydrogen or $NR_5R_6$, and $R_1$, $R_2$, $R_5$ and $R_6$ are selected from hydrogen, alkyl, aryl, and cycloalkyl:

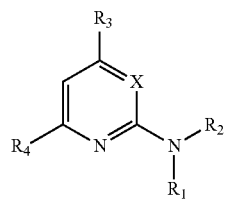

These compounds can promote the differentiation of undifferentiated skeletal muscle progenitor cells and pluripotent stem cells into cardiomyocyte-like cells.

At the same time, it is known that retinoic acid (RA) influences cell differentiation during the development of embryos by binding to certain retinoic acid receptors (RAR, RXR). As a result, research has delved into small molecules which are also able to bind to these receptors. In doing so, Peterson et al., PloS ONE 3(4), e1947 (2008), have found in zebrafish model experiments that 3-[(4.6-diphenoxy-1,3,5-triazin-2-yl)amino]benzoic acid (DTAB) has a substantial influence on the formation of the anterior-posterior (A-P) axis and organ development in embryos. Therefrom, it was concluded that this small molecule obviously docks onto the receptors RARβ and RARγ and activates the retinoic acid signaling pathway.

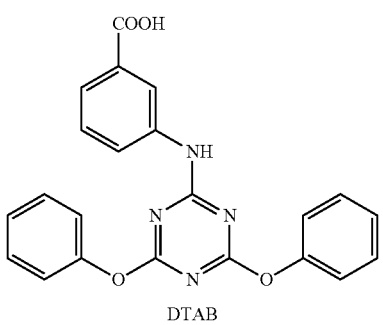 [SMILES: O=C(O)c1cccc(Nc2nc(Oc3ccccc3)nc(Oc3ccccc3)n2)c1]

DTAB

However, the physiological effects of such treatment with this anilinophenoxytriazine were serious defects in A-P axis formation and the formation of the brain, heart and vessels, which resulted in embryos for which no phenotype could be identified at all.

Against this backdrop, it was an aim of the invention to synthesize other triazines having beneficial effects on cell differentiation, in particular such having an enhanced cardiogenic effect.

DISCLOSURE OF THE INVENTION

The invention achieves this goal by providing the use of anilino- and/or phenoxytriazines of the following formula (I) for inducing the differentiation of mammalian cells into cardiomyocyte-like cells:

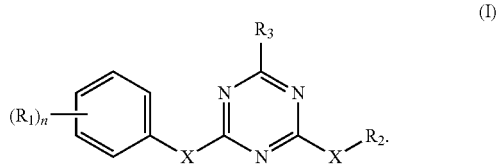

(I)

wherein:
each X is independently —$NR_4$— or —O—, wherein $R_4$ is selected from hydrogen and $C_{1-6}$-alkyl;
$R_1$ is selected from hydroxy, $C_{1-6}$-alkoxy, carboxy, $C_{1-6}$-alkoxycarbonyl, halo, cyano, nitro, formyl, amino, $C_{1-6}$-alkylamino and di-$C_{1-6}$-alkylamino, in which each $C_{1-6}$-alkyl or -alkoxy residue is optionally further substituted with one or more $R_5$ substituents, with $R_5$ being selected from hydroxy, halo, cyano, and nitro;
n is 0 to 5;
$R_2$ is selected from hydrogen, aryl, heteroaryl, and $C_{1-6}$-alkyl, in which an aryl or heteroaryl residue is optionally further substituted with one or more $R_6$ substituents, where the same options apply for $R_6$ as for $R_1$ and where a $C_{1-6}$-alkyl is optionally further substituted with one or more $R_5$ substituents; and
$R_3$ is selected from hydrogen, halo, $NR_4R_7$, $OR_7$, $SR_7$, and $R_7$, where the same options apply for $R_7$ as for $R_2$;
by incubating the cells with one or more compounds of formula (I).
with the proviso that the compound of formula (I) is not 3-[(4.6-diphenoxy-1,3,5-triazin-2-yl)amino]benzoic acid.
That is to say, the inventors have surprisingly found in model experiments that many of these anilino- or phenoxytriazines are able to promote the differentiation of murine cells (P19 and/or C2C12 cells) into cardiomyocyte-like cells. Based on the above-mentioned experiences with DTAB, the positive results for derivatives of this compound were particularly surprising: excellent differentiation promotion was observed even with only slight modifications of DTAB.

On the other hand, it has been shown that the smallest differences, e.g. the position of a substituent on one and the same phenyl residue, may have detrimental effects. The following preferences therefore simply reflect the inventors' experiences so far, which will have to be completed in further research.

Thus, in some preferred embodiments of the invention, $R_1$ is selected from t-butyl, methoxy, hydroxymethyl, carboxy, methoxycarbonyl, t-butoxycarbonyl, cyano, formyl, nitro, and chloro. In some preferred embodiments, $R_2$ is selected from phenyl, ethyl, and propyl. In some preferred embodiments, $R_3$ is selected from hydrogen, chloro, —$NR_4R_7$, and $R_7$, with $R_4$ and $R_7$ being defined as above. In some preferred embodiments, $R_4$ is hydrogen. In some preferred embodiments, $R_5$ is hydroxy. In some preferred embodiments, $R_6$ is selected from t-butyl, methoxy, hydroxymethyl, carboxy, methoxycarbonyl, t-butoxycarbonyl, cyano, formyl, nitro, and chloro. In some preferred embodiments, $R_7$ is phenyl optionally substituted with one or two $R_6$ substituents, with $R_6$ being defined as above.

In particularly preferred embodiments, both X are either —O— or —NH—. Even more preferably, both X are —O— and $R_3$ is $NHR_7$, with $R_7$ being defined as above.

Even more preferably, the compound of formula (I) is an anilinodiphenoxytriazine of the following formula (II), which is optionally substituted with one or more $R_1$, $R_6$ and/or $R_7$ substituents at one or more of the three phenyl groups, with $R_1$, $R_6$ and $R_7$ being as defined above and n, m and o each being independently 0 to 5:

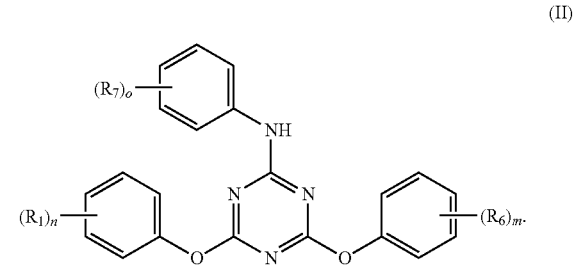

(II)

Alternatively, both X are —NH— and $R_3$ is hydrogen or chloro. The subscripts n, m and o, if present, are each independently 0, 1, or 2.

Particularly preferably, the compound of formula (I) is selected from the following compounds and mixtures thereof:
2-[4-chloro-6-(4-methoxyphenylamino)-1,3,5-triazin-2-ylamino]ethanol (1).
3-[4-chloro-6-(4-methoxyphenylamino)-1,3,5-triazin-2-ylamino]propan-1-ol (2).
3-{[4-(3-chlorophenoxy)-6-phenoxy-1,3,5-triazin-2-yl]amino}benzoic acid methyl ester (8).
3-{[4-(4-chlorophenoxy)-6-phenoxy-1,3,5-triazin-2-yl]amino}benzoic acid (29).
3-{[4-(3-chlorophenoxy)-6-phenoxy-1,3,5-triazin-2-yl]amino}benzoic acid (30).
3-{[4-(2-chlorophenoxy)-6-phenoxy-1,3,5-triazin-2-yl]amino}benzoic acid (31).

3-{[4-(4-t-butylphenoxy)-6-phenoxy-1,3,5-triazin-2-yl]
amino}benzoic acid (32).
3-{[4-(4-methoxyphenoxy)-6-phenoxy-1,3,5-triazin-2-yl]
amino}benzoic acid (33).
3-{[4-(4-cyanophenoxy)-6-phenoxy-1,3,5-triazin-2-yl]
amino}benzoic acid (34).
3-{[4-(3-nitrophenoxy)-6-phenoxy-1,3,5-triazin-2-yl]
amino}benzoic acid (35).
3-{[4-(4-formyl-2-methoxyphenoxy)-6-phenoxy-1,3,5-triazin-2-yl]amino}benzoic acid (36).
3-{[4-(4-cyanophenoxy)-6-(4-methoxyphenoxy)-1,3,5-triazin-2-yl]amino}benzoic acid (38).
{4-[(4.6-diphenoxy-1,3,5-triazin-2-yl)amino]
phenyl}methanol (39).
{3-[(4.6-diphenoxy-1,3,5-triazin-2-yl)amino]
phenyl}methanol (40).
{3-[(4-(3-chlorophenoxy)-6-phenoxy-1,3,5-triazin-2-yl)
amino]phenyl}methanol (42).
{3-[(4-(4-t-butylphenoxy)-6-phenoxy-1,3,5-triazin-2-yl)
amino]phenyl}methanol (44), and
{3-[(4-(4-methoxyphenoxy)-6-phenoxy-1,3,5-triazin-2-yl)
amino]phenyl}methanol (45).

Even more preferably, the compound of formula (I) is selected from the following compounds and mixtures thereof:
3-[4-chloro-6-(4-methoxyphenylamino)-1,3,5-triazin-2-ylamino]propan-1-ol (2).
3-{[4-(3-chlorophenoxy)-6-phenoxy-1,3,5-triazin-2-yl]
amino}benzoic acid methyl ester (8).
3-{[4-(4-chlorophenoxy)-6-phenoxy-1,3,5-triazin-2-yl]
amino}benzoic acid (29).
3-{[4-(3-chlorophenoxy)-6-phenoxy-1,3,5-triazin-2-yl]
amino}benzoic acid (30).
3-{[4-(2-chlorophenoxy)-6-phenoxy-1,3,5-triazin-2-yl]
amino}benzoic acid (31).
3-{[4-(3-nitrophenoxy)-6-phenoxy-1,3,5-triazin-2-yl]
amino}benzoic acid (35).
3-{[4-(4-formyl-2-methoxyphenoxy)-6-phenoxy-1,3,5-triazin-2-yl]amino}benzoic acid (36).
3-{[4-(4-cyanophenoxy)-6-(4-methoxyphenoxy)-1,3,5-triazin-2-yl]amino}benzoic acid (38).
{4-[(4.6-diphenoxy-1,3,5-triazin-2-yl)amino]
phenyl}methanol (39), and
{3-[(4-(4-t-butylphenoxy)-6-phenoxy-1,3,5-triazin-2-yl)
amino]phenyl}methanol (44).

In particular, the compound of formula (I) is selected from the following compounds and mixtures thereof:
3-{[4-(4-chlorophenoxy)-6-phenoxy-1,3,5-triazin-2-yl]
amino}benzoic acid (29).
3-{[4-(4-formyl-2-methoxyphenoxy)-6-phenoxy-1,3,5-triazin-2-yl]amino}benzoic acid (36).
{4-[(4.6-diphenoxy-1,3,5-triazin-2-yl)amino]
phenyl}methanol (39), and
{3-[(4-(4-t-butylphenoxy)-6-phenoxy-1,3,5-triazin-2-yl)
amino]phenyl}methanol (44).

The differing preferences are due to the test results, which are indicated in the following experimental part, as are the syntheses of numerous compounds of formula (I). They include, in addition to examples of the invention, inactive and/or toxic comparative examples. Specifically, in addition to DTAB as the reference substance 45, various novel compounds were prepared, 28 of which have so far been tested. 17 of these, i.e. more than 60%, showed positive efficiency. The fact that compounds of formula (I) may be used as catalysts in the differentiation of mammalian cells is thus proven beyond doubt in the examples. A person of skill in the art of organic synthesis will be able to synthesize other compounds of formula (I), which also exert the desired effect, without undue experimentation by following the instructions herein using his general knowledge in the art.

"$C_{1-6}$-alkyl" in the alkyl and alkoxy residues herein means linear, branched or cyclic, saturated or unsaturated, aliphatic carbon residues having 1 to 6 carbon atoms. Other expressions and abbreviations used in the examples are known in the art. In particular, Ph means phenyl, PE means petroleum ether, EtOAc means ethyl acetate, THF means tetrahydrofuran, DMSO means dimethyl sulfoxide, DIPEA means diisopropylethylamine, DC means thin-layer chromatography or chromatogram, and MPLC means medium-pressure liquid chromatography.

EXAMPLES

Reference Example 1

Preparation of 4,6-dichloro-N-(4-methoxyphenyl)-1,3,5-triazine-2-amine (A)

Cyanuric chloride (2,4,6-trichloro-1,3,5-triazine; 500 mg, 2.73 mmol) was heated to 50° C. in acetone (5 ml) and added to a mixture of crushed ice and water (10 ml), p-anisidine (4-methoxyaniline; 673 mg, 5.47 mmol) dissolved in water/acetone (1/1; 5 ml) was added dropwise with heavy stirring. After 2 hrs of stirring at 0° C., the obtained colorless suspension was filtered, washed with cold water, and dried under vacuum to give the title compound as colorless crystals (685 mg, 2.53 mmol, 93% of theory). Mp.: 165-168° C. ($H_2O$), RH: 0.61 (PE:EtOAc=5:1), $^1$H-NMR (CDCl$_3$, 200 MHz): δ=3.82 (s, 3H, OCH$_3$), 6.87-6.99 (m, 2H, H3'), 7.35-7.47 (m, 2H, H2'), 7.53 (s, 1H, NH), $^{13}$C-NMR (CDCl$_3$, 50 MHz): δ=55.5 (q), 114.5 (d, C2'), 123.5 (d, C3'), 128.4 (s, C1'), 157.8 (s, C4'), 164.2 (s, C4/C6) 170.1 (s, C4/C6), 171.3 (s, C2).

Reference Example 2

General Procedure A for Preparing Anilinodiphenoxytriazines

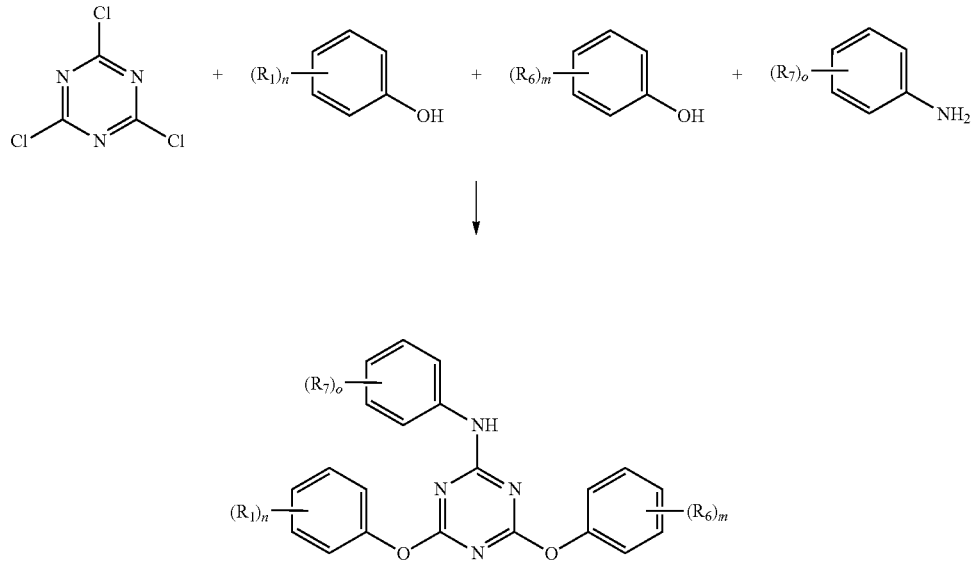

1 equivalent of component $(R_1)_n$PhOH was dissolved in an 8 ml test tube in THF (0.5 ml), and 1.1 equivalents of DIPEA were added. This solution was cooled down to −35° C. and added dropwise to 1 eq. of cyanuric chloride in THF (2 ml) while stirring. Residual component $(R_1)_n$PhOH was washed into the reaction mixture with another 0.5 ml of THF. Stirring was then performed at this temperature, until complete reaction (or no significant change of conversion) was observed by DC. A solution of 1 eq. of component $(R_6)_m$PhOH and 1.6 equivalents of DIPEA in THF (0.5 ml) was then added dropwise, again followed by rinsing with 0.5 ml of THF, and again stirred until completion. Afterwards, 1.5 equivalents of DIPEA, followed by 1.15 equivalents of component $(R_7)_o$PhNH$_2$ were added to the reaction mixture and stirred until completion.

For workup, CH$_2$Cl$_2$ (15 ml) and 1 N aqueous HCl (15 ml) were added to the mixture and shaken out. The organic layer was washed with water (2×15 ml) and concentrated in vacuo. Further purification is separately indicated for each individual case.

Reference Example 3

General Procedure B for Preparing Anilinodiphenoxytriazines

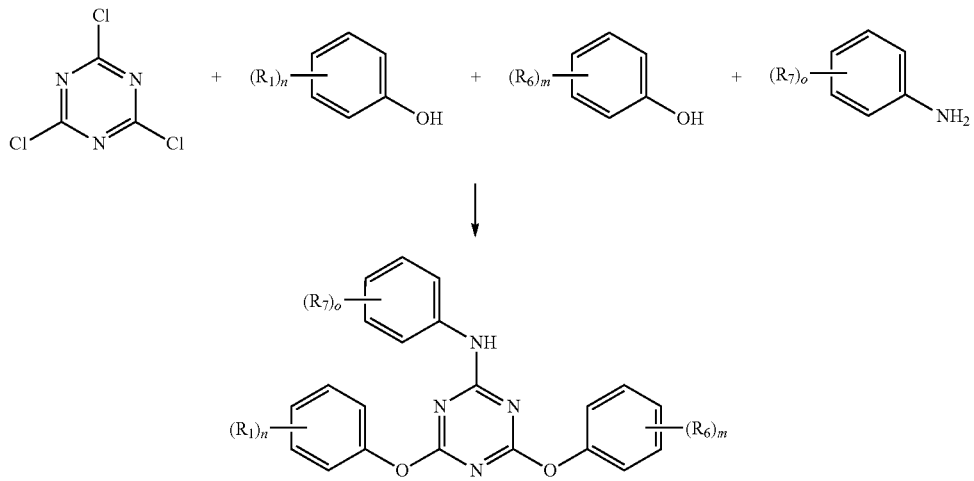

1 equivalent of component $(R_1)_n$PhOH was dissolved in an 8 ml test tube in THF (0.4 ml), and 1.1 equivalents of diisopropylamine (DIPEA) were added. This solution was cooled down to −35° C. and added dropwise to 1 eq. of cyanuric chloride in THF (0.7 ml) while stirring. Residual component $(R_1)_n$PhOH was washed into the reaction mixture with another 0.4 ml of THF. Stirring was then performed at this temperature, until complete reaction (or no significant change of conversion) was observed by DC. A solution of 1 eq. of component $(R_6)_m$PhOH and 1.6 equivalents of DIPEA in THF (0.4 ml) was then added dropwise, again followed by rinsing with 0.5 ml of THF, and again stirred until completion. Afterwards, 1.5 equivalents of DIPEA, followed by 1.15 equivalents of component $(R_7)_o$PhNH$_2$ were added to the reaction mixture and stirred until completion.

Workup was performed in two different ways:

B1: CH$_2$Cl$_2$ (10 ml) and water (10 ml) were added to the mixture and shaken out, while the aqueous phase was back-extracted with CH$_2$Cl$_2$ (2×15 ml). The combined organic layers were concentrated in vacuo. Further purification is separately indicated for each individual case.

B2: The reaction mixture was taken up in EtOAc (15 ml) and washed with 1 N aqueous HCl (2×10 ml), saturated aqueous NaHCO$_3$ solution (10 ml), and brine (10 ml). The organic layer was concentrated in vacuo.

Reference Example 4

General Procedure C for Preparing Anilinodiphenoxytriazines

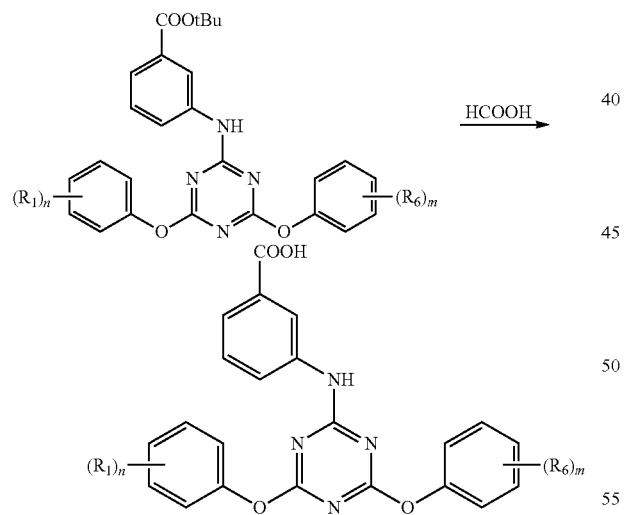

The respective t-butyl ester was treated with formic acid (4 ml) in an 8 ml test tube and sonicated until the starting material was dissolved. Stirring was then performed at the given temperature until complete reaction was observed by DC. The reaction mixture was transferred to a round-bottom flask while rinsing with a few milliliters of CH$_2$Cl$_2$. The solvents were then removed under reduced pressure, followed by the addition of Et$_2$O in order to facilitate removal of the residual formic acid, and the solvent was again evaporated. The residue was dried in vacuo.

Reference Example 5

Preparation of 3[(4.6-diphenoxy-1,3,5-triazin-2-yl)amino]benzoic acid (DTAB)

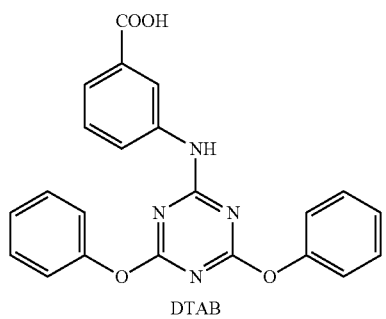 [SMILES: O=C(O)c1cccc(Nc2nc(Oc3ccccc3)nc(Oc3ccccc3)n2)c1]

DTAB

Preparation was performed according to the above general procedure C from 3-[(4.6-diphenoxy-1,3,5-triazin-2-yl)amino]benzoic acid t-butyl ester (21) (46 mg, 0.10 mmol) obtained in Example 18 below at 50° C. for 1 hr, whereby a slightly yellowish solid was obtained (40 mg, quantitative). Mp.: 276.5-270° C. (Et$_2$O), RH: 0.57 (Hexane:EtOH=1:1), $^1$H-NMR (DMSO-d$_6$, 200 MHz): δ=7.14-7.35 (m, 7H), 7.38-7.52 (m, 4H), 7.56 (d, J$_3$=7.7 Hz, 1H), 7.76 (d, J$_3$=8.3 Hz, 1H), 8.03 (s, 1H, H2'), 10.40 (s, 1H, NH), 12.98 (bs, 1H, CO$_2$H), $^{13}$C-NMR (DMSO-d$_6$, 50 MHz): δ=121.5 (d, C2'), 121.8 (d, C2''+C2'''+C6''+C6'''), 124.1 (d, C4'), 124.8 (d, C6'), 125.7 (d, C4''+C4'''), 128.5 (d, C5'), 129.6 (d, C3''+C3'''+C5''+C5'''), 131.2 (s, C3'), 138.6 (s, C1'), 151.8 (s, C1'', C1'''), 166.2 (s, C2), 167.1 (s, CO$_2$), 171.8+172.2 (bs, C4+C6, rotamers). MW calcd. for C$_{14}$H$_{16}$N$_4$O$_4$: 400.39 g/mol.

Reference Example 6

General Procedure D for Preparing Anilinodiphenoxytriazines

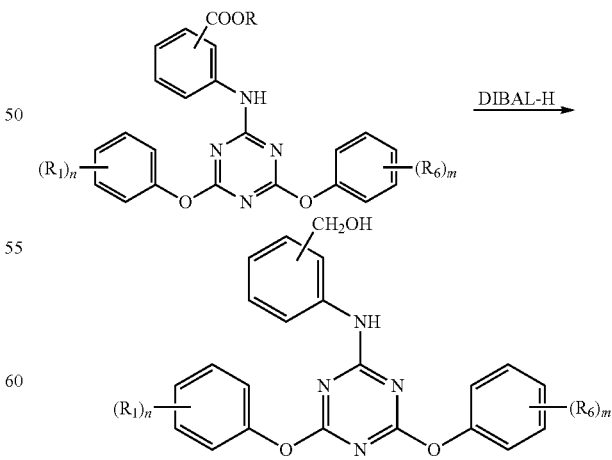

An 8 ml test tube was filled with the respective ester and sealed, and the atmosphere inside was replaced by argon using the Schlenk technique. Anhydrous CH$_2$Cl$_2$ (1 ml) was filled in using a syringe, and the contents were stirred until the ester was dissolved, and then cooled to −70° C. with liquid nitrogen in a MeOH bath. A solution of diisobutyl aluminum hydride in n-hexane (DIBAL-H, 0.86 mmol/ml) was then slowly added. The reaction mixture was stirred until complete reaction was observed by DC (for which in some cases additional DIBAL-H solution needed to added). The reaction was then quenched by adding 1 N aqueous HCl (1 ml), stirred for another 5 min and then removed from the cooling bath, followed by the addition of water (10 ml). After extraction with $CH_2Cl_2$ (10 ml, then another 2×5 ml), the solvent was removed in vacuo, and the respective compound was further purified as indicated.

Example 1

Preparation of 2-[4-chloro-6-(4-methoxyphenylamino)-1,3,5-triazin-2-ylamino]ethanol (1)

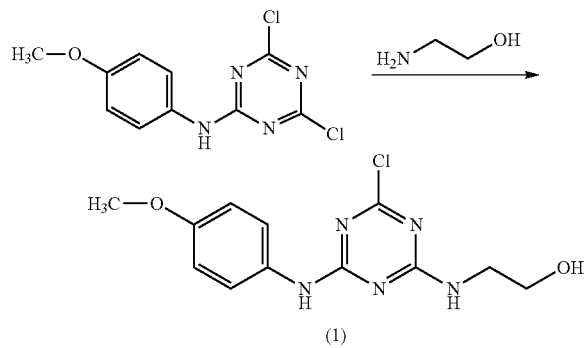

Compound (A) from Reference Example 1 (101 mg, 0.37 mmol), ethanolamine (25.1 mg, 0.41 mmol) and DIPEA (52.9 mg, 0.41 mmol) were dissolved in dioxane (2 ml) and stirred at room temperature for 4 hrs. By evaporating the dioxane, a crude product was obtained, which was purified by column chromatography (PE:EtOAc=1:2), which gave the title compound as a colorless solid (72 mg, 0.24 mmol, 66% of theory). Mp.: 169-173° C. (PE:EtOAc), RH: 0.36 (PE:EtOAc=1:2), $^1$H-NMR (CD$_3$OD, 200 MHz): δ=3.49 (t, J=5.58 Hz, 2H, CH$_2$), 3.67 (q, J=5.61 Hz, 2H, CH$_2$), 3.78 (s, 3H, OCH$_3$), 6-81-6.94 (m, 2H, H2'), 7.50 (d, J=7.82 Hz, 2H, H3'), $^{13}$C-NMR (CD$_3$OD, 200 MHz): δ=44.1 (t, CH$_2$), 44.3 (t, CH$_2$), 55.9 (q, OCH$_3$), 61.3 (t), 61.7 (t), 114.8 (d), 123.7 (d), 123.9 (d), 132.7 (s), 132.7 (s), 132.8 (s), 157.7 (s). HR-MS: calcd. [MH]$^+$=296.0909; found [MH]$^+$=296.0920.

Example 2

Preparation of 3-[4-chloro-6-(4-methoxyphenylamino)-1,3,5-triazin-2-ylamino]propan-1-ol (2)

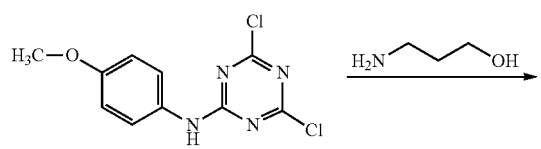

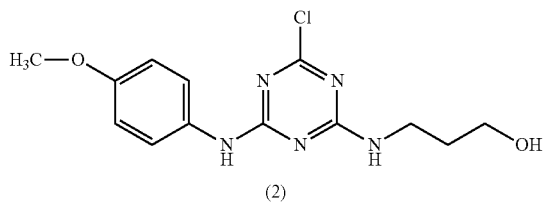

Reaction was analogous to example 1 with a 10% molar excess of propanolamine instead of ethanolamine, giving the title compound as a colorless solid (69% of theory). Mp.: 155-159° C. (PE/EtOAc), RH: 0.30 (PE:EtOAc=1:2), $^1$H-NMR (CD$_3$OD, 200 MHz): δ=1.81 (quin, J=6.47 Hz, 2H, CH$_2$), 3.45 (q, J=6.71 Hz, 2H, CH$_2$), 3.62 (t, J=6.26 Hz, 2H, CH$_2$), 3.78 (s, 3H, OCH$_3$), 6.81-6.94 (m, 2H, H2'), 7.43-7.46 (m, 2H, H3'), $^{13}$C-NMR (CD$_3$OD, 200 MHz): δ=31.2 (t, CH$_2$), 36.8 (t, CH$_2$), 37.3 (t, CH$_2$), 54.0 (q, OCH$_3$), 58.5 (t), 58.6 (t), 113.0 (d), 121.9 (d), 122.1 (d), 130.9 (s), 155.8 (s). HR-MS: calcd. [MH]$^+$=310.1065; found [MH]$^+$=310.1074.

Example 3

Preparation of 6-chloro-N$_2$-ethyl-N$_4$-(4-methoxyphenyl)-1,3,5-triazin-2.4-diamine (3)

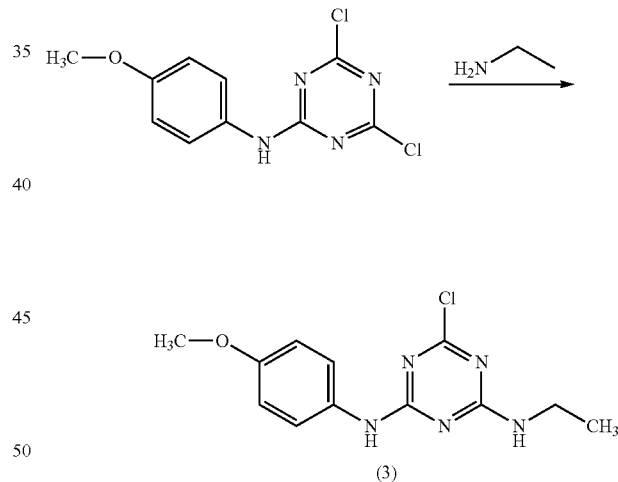

Reaction was analogous to example 1 with a 10% molar excess of ethylamine instead of ethanolamine, giving the title compound as a colorless solid (71% of theory). Mp.: 174-176° C. (PE/EtOAc), RH: 0.43 (PE:EtOAc=1:1), $^1$H-NMR (CDCl$_3$, 200 MHz): δ=1.16-1.29 (m, 3H, CH$_3$), 2.05 (d, J=3.7 Hz, 1H, NH), 3.37-3.56 (m, 2H, CH$_2$), 3.81 (s, 3H, OCH$_3$), 5.78 (s, 1H, NH), 6.83-6.94 (m, 2H, H2'), 7.33-7.53 (m, 2H, H3'), $^{13}$C-NMR (CDCl$_3$, 200 MHz): δ=14.5 (q), 36.1 (t), 55.5 (q), 114.1 (d), 122.3 (d), 123.3 (d), 130.6 (s) HR-MS: calcd. [MH]$^+$=280.0965; found [MH]$^+$=280.0967.

Example 4

Preparation of 2-[4-(4-methoxyphenylamino)-1,3,5-triazin-2-ylamino]ethanol (4)

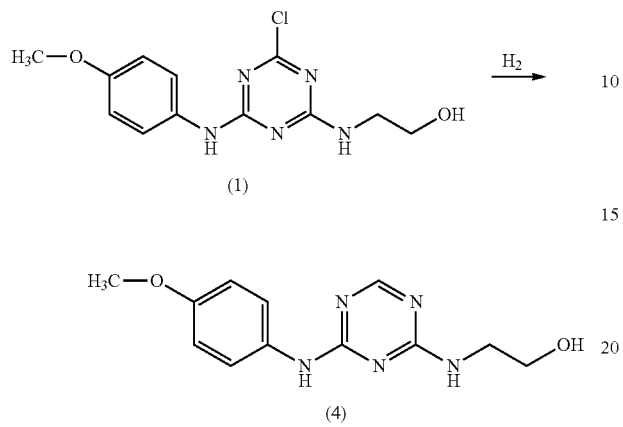

Compound (1) (50 mg, 0.17 mmol) and palladium/active carbon (5 mg) were stirred overnight at room temperature in dry methanol (20 ml) under a hydrogen atmosphere. The catalyst was then filtered off and the solvent distilled off to give the title compound as a colorless solid (37 mg, 0.14 mmol, 84% of theory). Mp.: 160-164° C. (MeOH), RH: 0.24 (EtOAc), $^1$H-NMR (CD$_3$OD, 200 MHz): δ=3.58 (t, J=4.1 Hz, 2H, CH$_2$), 3.73 (t, J=4.4 Hz, 2H, CH$_2$), 3.81 (s, 3H, OCH$_3$), 6.96 (d, J=8.4 Hz, 2H, H2'), 7.52 (s, 2H, H3'), 8.23 (s, 1H, H6), $^{13}$C-NMR (CD$_3$OD, 200 MHz): δ=43.7 (t, CH$_2$), 55.2 (q, OCH$_3$), 59.8 (t, CH$_2$), 114.4 (d, C2'), 124.1 (d, C3'), 156.6 (d, C6), 158.3 (s), 159.5 (s). HR-MS: calcd. [MH]$^+$=264.1455; found [MH]$^+$=264.1453.

Example 5

Preparation of 4-[(4.6-diphenoxy-1,3,5-triazin-2-yl)amino]benzoic acid ethyl ester (5)

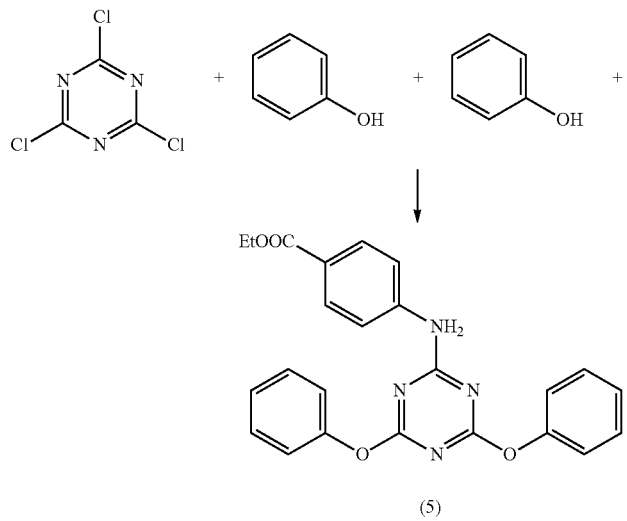

This compound was prepared according to the above general procedure A.

Step 1: cyanuric chloride (277 mg, 1.50 mmol), phenol (141 mg, 1.50 mmol), DIPEA (213 mg, 1.65 mmol); −35° C. for 6 hrs.

Step 2: Phenol (141 mg, 1.50 mmol), DIPEA (310 mg, 2.40 mmol); 35° C. for 46 hrs.

Step 3: 4-aminobenzoic acid ethyl ester (285 mg, 1.73 mmol), DIPEA (291 mg, 2.25 mmol); 40° C. for 42 hrs.

After workup according to the general procedure A, Et$_2$O (1 ml) and PE (2 ml) were added to provide for precipitation of the product and to accelerate drying. The crude mixture was dissolved in a boiling mixture of CHCl$_3$ and PE (1:2, 12 ml), and n-hexane (8 ml) was added. After overnight crystallization, the compound was filtered off, washed with PE (40 ml) and dried in vacuo. This gave a colorless solid (611 mg, 95% of theory). Mp.: 159-161° C. (PE), RH: 0.54 (hexane:EtOAc=2:1), $^1$H-NMR (DMSO-d$_6$, 200 MHz): δ=1.28 (t, J$_3$=7.1 Hz, 3H, CH$_3$), 4.25 (q, J$_3$=7.1 Hz, 2H, CH$_2$), 7.26-7.35 (m, 6H), 7.45-7.57 (m, 6H), 7.63-7.74 (m, 2H), 10.57 (s, 1H, NH), $^{13}$C-NMR (DMSO-d$_6$, 50 MHz): δ=14.1 (q, CH$_3$), 60.4 (t, CH$_2$), 119.4 (d, C2'+C6'), 121.9 (d, C2"+C2"'+C6"+C6"'), 123.9 (s, C4'), 125.8 (d, C4"+C4"'), 129.60 (C3'+C5'), 129.63 (d, C3"+C3"'+C5"+C5"'), 143.0 (s, C1'), 151.9 (s, C1"+C1"'), 165.3 (s, CO$_2$), 166.0 (s, C2), 172.1 (s, C4+C6, single rotamers not recognizable). MW calcd. for C$_{24}$H$_{20}$N$_4$O$_4$: 428.44 g/mol.

Example 6

Preparation of 3-[(4.6-diphenoxy-1,3,5-triazin-2-yl)amino]benzoic acid methyl ester (6)

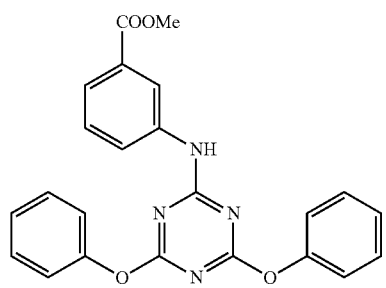 [SMILES: O=C(O)c1cccc(Nc2nc(Oc3ccccc3)nc(Oc3ccccc3)n2)c1]

Preparation was performed according to the general procedure A in a similar manner to example 5.

Step 1: cyanuric chloride (277 mg, 1.50 mmol), phenol (141 mg, 1.50 mmol), DIPEA (213 mg, 1.65 mmol); −35° C. for 6 hrs.

Step 2: phenol (141 mg, 1.50 mmol), DIPEA (310 mg, 2.40 mmol); 35° C. for 46 hrs.

Step 3: 3-aminobenzoic acid methyl ester (261 mg, 1.73 mmol), DIPEA (291 mg, 2.25 mmol); 35° C. for 26 hrs.

After workup according to the general procedure A, the compound was crystallized. For recrystallization, it was dissolved in boiling CHCl$_3$ (10 ml), and for precipitation, n-hexane (10 ml) was added. After crystallization overnight, the target compound was filtered off, washed with PE (30 ml) and dried in vacuo. This gave a slightly yellowish powder (523 mg, 84% of theory). Mp.: 198-199.5° C. (PE), RH: 0.50 (hexane:EtOAc=2:1), $^1$H-NMR (DMSO-d$_6$, 200 MHz): δ=3.81 (s, 3H, CH$_3$), 7.18-7.31 (m, 7H), 7.41-7.48 (m, 4H), 7.56 (d, J$_3$=7.8 Hz, 1H), 7.75 (d, J$_3$=7.9 Hz, 1H), 8.03 (s, 1H, H2'), 10.42 (s, 1H, NH), $^{13}$C-NMR (DMSO-d$_6$, 50 MHz): δ=52.2 (q, CH$_3$), 121.2 (d, C2'), 121.8 (d, C2"+C2'"+C6"+C6'"), 123.9 (d, C4'), 125.1 (d, C6'), 125.7 (d, C4"+C4'"), 128.7 (d, C5'), 129.6 (d, C3"+C3'"+C5"+C5'"), 130.0 (s, C3'), 138.9 (s, C1'), 151.8 (s, C1", C1'"), 166.0 (s, C2*), 166.2 (s, CO$_2$*), 171.8+172.2 (bs, C4+C6, rotamers). MW calcd. for C$_{23}$H$_{18}$N$_4$O$_4$: 414.41 g/mol.

Example 7

Preparation of 3-{[4-(4-chlorophenoxy)-6-phenoxy-1,3,5-triazin-2-yl]amino}benzoic acid methyl ester (7)

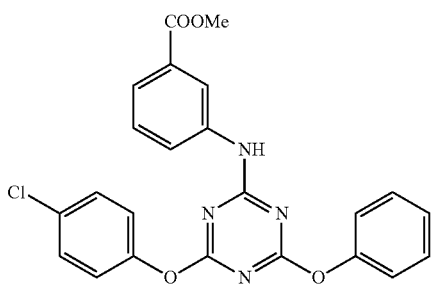

Preparation was performed according to the general procedure A.

Step 1: cyanuric chloride (277 mg, 1.50 mmol), phenol (141 mg, 1.50 mmol), DIPEA (213 mg, 1.65 mmol); −35° C. for 6 hrs.

Step 2: 4-chlorophenol (193 mg, 1.50 mmol), DIPEA (310 mg, 2.40 mmol); 35° C. for 46 hrs.

Step 3: 3-aminobenzoic acid methyl ester (261 mg, 1.73 mmol), DIPEA (291 mg, 2.25 mmol); 35° C. for 26 hrs.

After workup according to the general procedure A, PE (5 ml) was added. The crude product was dissolved in boiling CHCl$_3$ (5.5 ml), and n-hexane (5.5 ml) was added. For accelerating crystallization, the mixture was briefly sonicated. The title compound was filtered off, washed with PE (15 ml) and dried in vacuo. This gave a colorless powder (546 mg, 81% of theory). Mp.: 186.5-188° C. (PE), RH: 0.48 (hexane:EtOAc=2:1), $^1$H-NMR (DMSO-d$_6$, 400 MHz): δ=3.82 (s, 3H, CH$_3$), 7.19-7.36 (m, 6H), 7.41-7.53 (m, 4H), 7.58 (d, J$_3$=6 Hz, 1H), 7.76 (bs, 1H), 8.08 (s, 1H, H2'), 10.47 (s, 1H, NH), $^{13}$C-NMR (DMSO-d$_6$, 100 MHz, 120° C.): δ=51.2 (q, CH$_3$), 120.9 (d), 121.2 (d), 123.5 (d), 124.8 (d), 127.6 (d), 128.6 (d), 128.7 (d), 129.3 (s), 129.9 (s), 138.1 (s, C1'), 150.3 (s, C1"), 151.6 (s, C1'"), 164.5 (s, C2*), 166.1 (s, CO$_2$*), 171.3+171.5 (s, C4+C6). A d signal was missing, probably due to overlapping. MW calcd. for C$_{23}$H$_{17}$ClN$_4$O$_4$: 448.86 g/mol.

Example 8

Preparation of 3-{[4-(3-chlorophenoxy)-6-phenoxy-1,3,5-triazin-2-yl]amino}benzoic acid methyl ester (8)

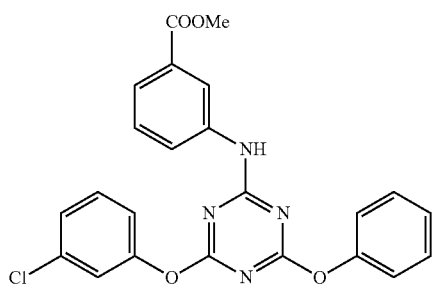 [SMILES: COC(=O)c1cccc(Nc2nc(Oc3ccccc3)nc(Oc3cccc(Cl)c3)n2)c1]

Preparation was performed according to the general procedure A.

Step 1: cyanuric chloride (277 mg, 1.50 mmol), phenol (141 mg, 1.50 mmol), DIPEA (213 mg, 1.65 mmol); −35° C. for 6 hrs.

Step 2: 4-chlorophenol (193 mg, 1.50 mmol), DIPEA (310 mg, 2.40 mmol); 35° C. for 46 hrs.

Step 3: 3-aminobenzoic acid methyl ester (261 mg, 1.73 mmol), DIPEA (291 mg, 2.25 mmol); 35° C. for 26 hrs, After workup according to the general procedure A, PE (5 ml) was added. The crude product was dissolved in boiling CHCl$_3$ (4 ml), and n-hexane (4 ml) was added. After cooling down and crystallization, the target compound was filtered off, washed with PE (20 ml) and dried in vacuo. This gave a colorless powder (600 mg, 89% of theory). Mp.: 151.5-156° C. (PE), RH: 0.55 (hexane:EtOAc=2:1), $^1$H-NMR (DMSO-d$_6$, 200 MHz): δ=3.81 (s, 3H, CH$_3$), 7.24-7.51 (m, 10H), 7.58 (d, J$_3$=7.8 Hz, 1H), 7.77 (d, J$_3$=8.3 Hz, 1H), 8.05 (t, J=1.6 Hz, 1H, H2'), 10.48 (s, 1H, NH), $^{13}$C-NMR (DMSO-d$_6$, 50 MHz): δ=52.2 (q, CH$_3$), 120.7 (d, C6"), 121.3 (d, C2'), 121.8 (d, C2"+C6'"), 122.4 (d, C2"), 124.0 (d, C4'), 125.1 (d, C6'), 125.7 (d, C4'"), 125.9 (d, C4"), 128.7 (d, C5'), 129.6 (d, C3'"+C5'"), 130.0 (s, C3'), 130.9 (d, C5"), 133.4 (s, C3"), 138.7 (s, C1'), 151.8 (s, C1'"), 152.4 (s, C1"), 166.0 (s, C2*), 166.2 (s, CO$_2$*), 171.3-172.4 (C4+C6, not resolved). MW calcd. for C$_{23}$H$_{17}$ClN$_4$O$_4$: 448.86 g/mol.

Example 9

Preparation of 3-{[4-(2-chlorophenoxy)-6-phenoxy-1,3,5-triazin-2-yl]amino}benzoic acid methyl ester (9)

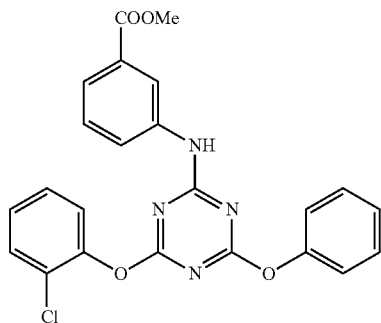 [SMILES: COC(=O)c1cccc(Nc2nc(Oc3ccccc3)nc(Oc3ccccc3Cl)n2)c1]

Preparation was performed according to the general procedure A.

Step 1: cyanuric chloride (277 mg, 1.50 mmol), phenol (141 mg, 1.50 mmol), DIPEA (213 mg, 1.65 mmol); −35° C. for 6 hrs.

Step 2: 4-chlorophenol (193 mg, 1.50 mmol), DIPEA (310 mg, 2.40 mmol); 35° C. for 46 hrs.

Step 3: 3-aminobenzoic acid methyl ester (261 mg, 1.73 mmol), DIPEA (291 mg, 2.25 mmol); 35° C. for 26 hrs.

After workup according to the general procedure A, PE (5 ml) was added. The crude product was dissolved in boiling CHCl$_3$ and n-hexane (2:3, 11 ml), and n-hexane (11 ml) was added. For accelerating crystallization, the mixture was briefly sonicated. After cooling down and crystallization, the target compound was filtered off, washed with PE (20 ml) and dried in vacuo. This gave a slightly yellowish powder (540 mg, 80% of theory). Mp.: 139-141.5° C. (PE), RH: 0.48 (hexane:EtOAc=2:1), $^1$H-NMR (DMSO-d$_6$, 200 MHz): δ=3.81 (s, 3H, CH$_3$), 7.17-7.48 (m, 9H), 7.58 (t, J$_3$=8.5 Hz, 2H), 7.69 (bs, 1H), 7.99 (s, 1H, H2'), 10.51 (s, 1H, NH), $^{13}$C-NMR (DMSO-d$_6$, 50 MHz): δ=52.2 (q, CH$_3$), 121.3 (d, C2'), 121.8 (d, C2'''+C6'''), 124.0 (d, C4'), 124.2 (d, C6''), 125.1 (d, C6'), 125.8 (d, C4'''), 126.0 (s, C2''), 127.5 (d, C4''*), 128.6 (d, C5''*), 128.7 (d, C5'*), 129.6 (d, C3'''+C5'''), 130.0 (s, C3'), 130.3 (d, C3''), 138.6 (s, C1'), 147.7 (s, C1''), 151.7 (s, C1'''), 166.0 (s, C2*), 166.2 (s, CO$_2$*), 171.2+171.6+171.9+172.2 (s, C4+C6, 2 pairs of rotamers). MW calcd. for C$_{23}$H$_{17}$ClN$_4$O$_4$: 448.86 g/mol.

Example 10

Preparation of 3-{[4-(4-t-butylphenoxy)-6-phenoxy-1,3,5-triazin-2-yl]amino}benzoic acid methyl ester (10)

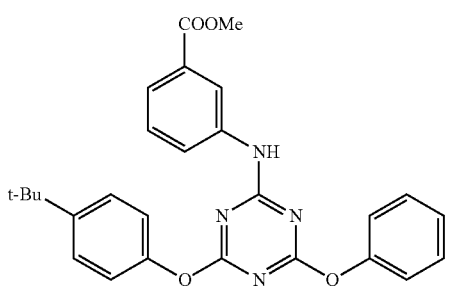 [SMILES: COC(=O)c1cccc(Nc2nc(Oc3ccccc3)nc(Oc3ccc(C(C)(C)C)cc3)n2)c1]

Preparation was performed according to the general procedure A.

Step 1: cyanuric chloride (277 mg, 1.50 mmol), phenol (141 mg, 1.50 mmol), DIPEA (213 mg, 1.65 mmol); −35° C. for 6 hrs.

Step 2: 4-chlorophenol (193 mg, 1.50 mmol), DIPEA (310 mg, 2.40 mmol); 35° C. for 46 hrs.

Step 3: 3-aminobenzoic acid methyl ester (261 mg, 1.73 mmol), DIPEA (291 mg, 2.25 mmol); 35° C. for 26 hrs, After workup according to the general procedure A, the solvent was completely evaporated, and the crude product was dissolved in boiling CHCl$_3$ and n-hexane (1:1, 4.5 ml), and n-hexane (8.5 ml) was added. For accelerating crystallization, the mixture was briefly sonicated. After cooling down and crystallization, the target compound was filtered off, washed with PE (60 ml) and dried in vacuo. This gave a colorless powder (565 mg, 80% of theory). Mp.: 85-86° C. (PE), RH: 0.53 (hexane:EtOAc=2:1), $^1$H-NMR (DMSO-d$_6$, 200 MHz): δ=1.28 (s, 9H, C(CH$_3$)$_3$), 3.82 (s, 3H, OCH$_3$), 7.14-7.30 (m, 6H), 7.41-7.48 (m, 4H), 7.56 (d, J$_3$=7.7 Hz, 1H), 7.76 (d, J$_3$=7.9 Hz, 1H), 8.04 (s, 1H, H2'), 10.41 (s, 1H, NH), $^{13}$C-NMR (DMSO-d$_6$, 50 MHz): δ=31.2 (q, C(CH$_3$)$_3$), 34.2 (s, C(CH$_3$)$_3$), 52.2 (OCH$_3$), 121.2 (d, C2''+C6''), 121.3 (d, C2'), 121.8 (d, C2'''+C6'''), 123.9 (d, C4'), 125.1 (d, C6'), 125.7 (d, C4'''), 126.3 (d, C3''+C5''), 128.7 (d, C5'), 129.6 (d, C3'''+C5'''), 130.0 (s, C3'), 138.9 (s, C1'), 148.0 (s, C4''*), 149.5 (s, C1'*), 151.8 (s, C1'''), 166.0 (s, C2*), 166.2 (s, CO$_2$*), 171.7-172.5 (C4+C6, not resolved). MW calcd. for C$_{27}$H$_{26}$N$_4$O$_4$: 470.52 g/mol.

Example 11

Preparation of 3-{[4-(4-methoxyphenoxy)-6-phenoxy-1,3,5-triazin-2-yl]amino}benzoic acid methyl ester (11)

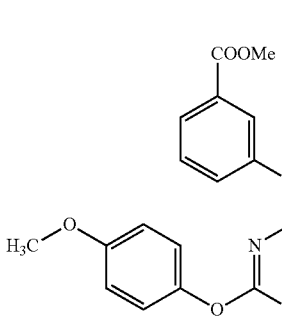

Preparation was performed according to the general procedure A.

Step 1: cyanuric chloride (277 mg, 1.50 mmol), phenol (141 mg, 1.50 mmol), DIPEA (213 mg, 1.65 mmol); −35° C. for 7 hrs.

Step 2: 4-chlorophenol (186 mg, 1.50 mmol), DIPEA (310 mg, 2.40 mmol); 35° C. for 47 hrs.

Step 3: 3-aminobenzoic acid methyl ester (261 mg, 1.73 mmol), DIPEA (291 mg, 2.25 mmol); 35° C. for 23.5 hrs, After workup according to general procedure A, the crude product was purified by column chromatography (silica gel, EtOAc/PE) and dried in vacuo. This gave a colorless solid (569 mg, 85% of theory). Mp.: 56-60° C. (EtOAc/PE), RH: 0.36 (hexane:EtOAc=2:1), $^1$H-NMR (DMSO-d$_6$, 200 MHz): δ=3.76 (s, 3H, C4''OCH$_3$), 3.81 (s, 3H, CO$_2$CH$_3$), 6.96 (d, J=9.0 Hz, 2H, H3"+H5"), 7.13-7.31 (m, 6H), 7.41-7.48 (m, 2H), 7.56 (d, $J_3$=7.9 Hz, 1H), 7.76 (d, J=7.9 Hz, 1H), 8.04 (s, 1H, H2'), 10.39 (s, 1H, NH), $^{13}$C-NMR (DMSO-$d_6$, 50 MHz): δ=52.1 (q, CO$_2$CH$_3$), 55.4 (q, C4"OCH$_3$), 114.4 (d, C3"+C5"), 121.1 (d, C2'), 121.7 (d, C2'"+C6'"), 122.6 (d, C2"+C6"), 123.8 (d, C4'), 125.0 (d, C6'), 125.6 (d, C4'"), 128.6 (d, C5'), 129.5 (d, C3'"+C5'"), 129.9 (s, C3'), 138.8 (s, C1'), 145.2 (s, C1"), 151.8 (s, C1'"), 156.8 (s, C4"), 165.9 (s, C2*), 166.1 (s, CO$_2$*), 171.7-172.5 (C4+C6, not resolved). MW calcd. for $C_{24}H_{20}N_4O_5$: 444.44 g/mol.

Example 12

Preparation of 3-{[4-(4-cyanophenoxy)-6-phenoxy-1,3,5-triazin-2-yl]amino}benzoic acid methyl ester (12)

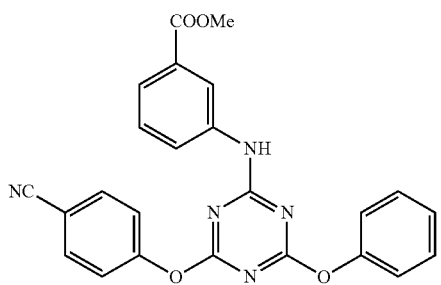

Preparation was performed according to the general procedure A.

Step 1: cyanuric chloride (277 mg, 1.50 mmol), phenol (141 mg, 1.50 mmol), DIPEA (213 mg, 1.65 mmol); −35° C. for 6 hrs.

Step 2: 4-chlorophenol (193 mg, 1.50 mmol), DIPEA (310 mg, 2.40 mmol); 35° C. for 46 hrs.

Step 3: 3-aminobenzoic acid methyl ester (261 mg, 1.73 mmol), DIPEA (291 mg, 2.25 mmol); 35° C. for 26 hrs, After workup according to the general procedure A, PE (10 ml) was added. The crude product was dissolved in boiling CHCl$_3$ (16 ml), and n-hexane (16 ml) was added. For accelerating crystallization, the mixture was briefly sonicated. After cooling down and crystallization, the target compound was filtered off, washed with PE (20 ml) and dried in vacuo. This gave a colorless powder (569 mg, 86% of theory). Mp.: 116.5-120° C. (PE), RH: 0.40 (hexane:EtOAc=2:1), $^1$H-NMR (DMSO-$d_6$, 200 MHz): δ=3.82 (s, 3H, CH$_3$), 7.24-7.31 (m, 4H), 7.41-7.60 (m, 5H), 7.71 (bs, 1H), 7.94 (d, $J_3$=8.1 Hz, 2H, H3"+H5"), 8.03 (s, 1H, H2'), 10.50 (s, 1H, NH), $^{13}$C-NMR (DMSO-$d_6$, 50 MHz): δ=52.1 (q, CH$_3$), 108.5 (s, C4"), 118.4 (s, CN), 121.2 (d, C2'), 121.7 (d, C2"'+C6'"), 123.2 (d, C2"+C6"), 124.0 (d, C4'), 125.1 (d, C6'), 125.7 (d, C4'"), 128.6 (d, C5'), 129.5 (d, C3'"+C5'"), 129.9 (s, C3'), 134.0 (d, C3"+C5"), 138.5 (s, C1'), 151.7 (s, C1'"), 155.1 (s, C1"), 165.8 (s, C2*), 166.0 (s, CO$_2$*), 170.9-172.3 (C4+C6, not resolved). MW calcd. for $C_{24}H_{17}N_5O_4$: 439.42 g/mol.

Example 13

Preparation of 3-{[4-(3-nitrophenoxy)-6-phenoxy-1,3,5-triazin-2-yl]amino}benzoic acid methyl ester (13)

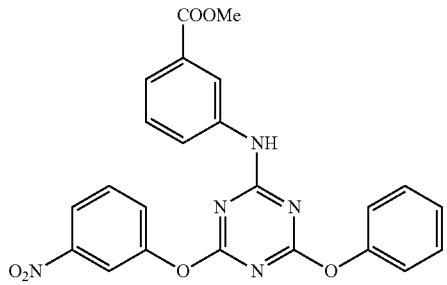

Preparation was performed according to the general procedure A.

Step 1: cyanuric chloride (277 mg, 1.50 mmol), phenol (141 mg, 1.50 mmol), DIPEA (213 mg, 1.65 mmol); −35° C. for 6 hrs.

Step 2: 4-chlorophenol (209 mg, 1.50 mmol), DIPEA (310 mg, 2.40 mmol); 40° C. for 46 hrs.

Step 3: 3-aminobenzoic acid methyl ester (261 mg, 1.73 mmol), DIPEA (291 mg, 2.25 mmol); 40° C. for 24 hrs, After workup according to general procedure A, Et$_2$O (5 ml) was added. The crude product was dissolved in boiling CHCl$_3$ (8 ml), and n-hexane (8 ml) was added. For accelerating crystallization, the mixture was briefly sonicated. After cooling down and crystallization, the target compound was filtered off and washed with PE (60 ml). The compound was then again dissolved in boiling CHCl$_3$ (17 ml) for recrystallization, and n-hexane (17 ml) was added. The recrystallized product was filtered off, washed with PE (25 ml) and dried in vacuo. This gave a colorless powder (474 mg, 69% of theory). Mp.: 165-176° C. (PE), RH: 0.34 (hexane:EtOAc=2:1), $^1$H-NMR (DMSO-$d_6$, 200 MHz): δ=3.80 (s, 3H, CH$_3$), 7.21-7.29 (m, 4H), 7.39-7.46 (m, 2H), 7.57 (d, $J_3$=7.5 Hz, 1H), 7.68-7.80 (m, 3H), 8.05 (s, 1H, H2'), 8.14 (d, $J_3$=7.3 Hz, 1H), 8.21 (s, 1H, H2"), 10.51 (s, 1H, NH), $^{13}$C-NMR (DMSO-$d_6$, 50 MHz): δ=52.1 (q, CH$_3$), 117.4 (d, C2"), 120.6 (d, C4"), 121.2 (d, C2'), 121.7 (d, C2'"+C6'"), 123.9 (d, C4'), 125.1 (d, C6'), 125.7 (d, C4'"), 128.6 (d, C6'"*), 128.7 (d, C5'*), 129.4 (d, C3'"+C5'"), 129.9 (s, C3'), 130.7 (d, C5"), 138.5 (s, C1'), 148.3 (s, C3"), 151.7 (s, C1"*), 151.9 (s, C1"*), 165.8 (s, C2*), 166.1 (s, CO$_2$*), 171.1-172.3 (C4+C6, not resolved). MW calcd. for $C_{23}H_{17}N_6O_6$: 459.41 g/mol.

Example 14

Preparation of 3-{[4-(4-formyl-2-methoxyphenoxy)-6-phenoxy-1,3,5-triazin-2-yl]-amino}benzoic acid methyl ester (14)

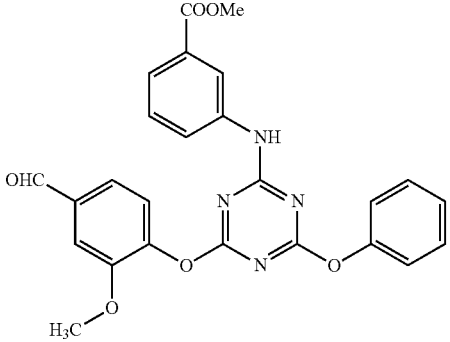

Preparation was performed according to the general procedure A.

Step 1: cyanuric chloride (277 mg, 1.50 mmol), phenol (141 mg, 1.50 mmol), DIPEA (213 mg, 1.65 mmol); −35° C. for 6 hrs.

Step 2: 4-chlorophenol (209 mg, 1.50 mmol), DIPEA (310 mg, 2.40 mmol); 40° C. for 46 hrs.

Step 3: 3-aminobenzoic acid methyl ester (261 mg, 1.73 mmol), DIPEA (291 mg, 2.25 mmol); 40° C. for 24 hrs.

After workup according to general procedure A, $Et_2O$ (2 ml) was added, followed by PE (5 ml). The crude product was purified by column chromatography (MPLC, 90 g silica gel, flow rate: 45 ml/min, $CH_2Cl_2$ with an EtOAc gradient of 1% to 4% over 60 min) and dried in vacuo. This gave colorless crystals (545 mg, 77% of theory). Mp.: 79-82° C. ($CH_2Cl_2$), RH: 0.24 (hexane:EtOAc=2:1), $^1$H-NMR (DMSO-$d_6$, 200 MHz): δ=3.80 (s, 3H, $CO_2CH_3$), 3.85 (s, 3H, C2"O$CH_3$), 7.17-7.30 (m, 4H), 7.40-7.70 (m, 7H), 7.99 (s, 1H, H2'), 10.00 (s, 1H, CHO), 10.46 (s, 1H, NH), $^{13}$C-NMR (DMSO-$d_6$, 50 MHz): δ=52.1 (q, $CO_2\underline{C}H_3$), 56.0 (q, C2"O$\underline{C}H_3$), 112.1 (d, C3"), 121.2 (d, C2'), 121.7 (d, C2'''+C6'''), 123.5 (d, C5"*), 123.7 (d, C4'*), 123.9 (d, C6"*), 125.0 (d, C6'), 125.7 (d, C4'"), 128.6 (d, C5'), 129.5 (d, C3'''+C5'''), 129.9 (s, C3'), 135.0 (s, C4"), 138.6 (s, C1'), 145.2 (s, C1"*), 151.68 (s, C2"*), 151.76 (s, C1'''*), 165.8 (s, C2*), 166.0 (s, $CO_2$*), 171.2-172.4 (C4+C6, not resolved), 191.9 (d, CHO). MW calcd. for $C_{26}H_{20}N_4O_6$: 472.45 g/mol.

Example 15

Preparation of 3-{[4-(4-formyl-2-methoxyphenoxy)-6-(4-methoxyphenoxy)-1,3,5-triazin-2-yl]amino}benzoic acid methyl ester (15)

(15)

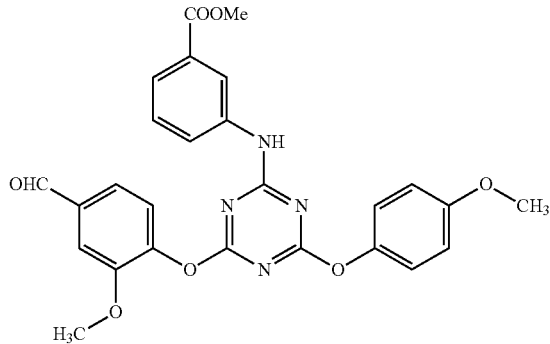

Preparation was performed according to general procedure A.

Step 1: cyanuric chloride (277 mg, 1.50 mmol), 4-Methoxyphenol (186 mg, 1.50 mmol), DIPEA (213 mg, 1.65 mmol); −35° C. for 7 hrs.

Step 2: 4-hydroxy-3-methoxybenzaldehyde (228 mg, 1.50 mmol), DIPEA (310 mg, 2.40 mmol); 40° C. for 47 hrs.

Step 3: 3-aminobenzoic acid methyl ester (261 mg, 1.73 mmol), DIPEA (291 mg, 2.25 mmol); 40° C. for 23.5 hrs.

After workup according to general procedure A, the crude product was purified by column chromatography (MPLC, 90 g of silica, flow rate 30-35 ml/min, $CH_2Cl_2$ with an EtOAc gradient of 1% to 20%) and dried in vacuo. This gave a colorless solid (545 mg, 77% of theory). Mp.: 79-82° C. ($CH_2Cl_2$), RH: 0.18 (hexane:EtOAc=2:1), $^1$H-NMR (DMSO-$d_6$, 200 MHz): δ=3.76 (s, 3H, C4'"O$CH_3$), 3.80 (s, 3H, $CO_2CH_3$*), 3.84 (s, 3H, C2"O$CH_3$*), 6.95 (d, $J_3$=9.0 Hz, 2H, H3'"+H5'"), 7.13-7.26 (m, 3H), 7.45-7.74 (m, 5H), 8.00 (s, 1H, H2'), 10.00 (s, 1H, CHO), 10.44 (s, 1H, NH), $^{13}$C-NMR (DMSO-$d_6$, 50 MHz): δ=52.1 (q, $CO_2\underline{C}H_3$), 55.4 (q, C4'"O$\underline{C}H_3$), 56.1 (q, C2"O$\underline{C}H_3$), 112.2 (d, C3"), 114.4 (d, C3'''+C5'''), 121.3 (d, C2'), 122.6 (d, C2'''+C6'''), 123.6 (d, C5"*), 123.8 (d, C4'*), 124.0 (d, C6"*), 125.1 (d, C6'), 128.7 (d, C5'), 130.0 (s, C3'), 135.0 (s, C4"), 138.7 (s, C1'), 145.2 (s, C1"*), 145.3 (s, C1'"*), 151.7 (s, C2"), 156.9 (s, C4'"), 166.0 (s, C2*), 166.2 (s, $CO_2$*), 171.5+172.3 (bs, C4+C6), 192.0 (d, CHO). MW calcd. for $C_{26}H_{22}N_4O_7$: 502.48 g/mol.

Example 16

Preparation of 3-{[4-(4-bromo-2-formylphenoxy)-6-(4-methoxyphenoxy)-1,3,5-triazin-2-yl]amino}benzoic acid methyl ester (16)

(16)

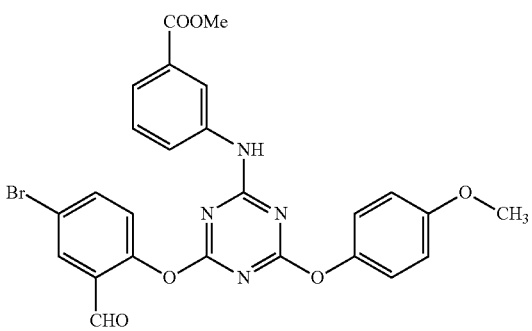

Preparation was performed according to general procedure A.

Step 1: cyanuric chloride (277 mg, 1.50 mmol), 4-methoxyphenol (186 mg, 1.50 mmol), DIPEA (213 mg, 1.65 mmol); −35° C. for 6 hrs.

Step 2: 5-bromo-2-hydroxybenzaldehyde (302 mg, 1.50 mmol), DIPEA (310 mg, 2.40 mmol); 40° C. for 46 hrs.

Step 3: 3-aminobenzoic acid methyl ester (261 mg, 1.73 mmol), DIPEA (291 mg, 2.25 mmol); 40° C. for 24 hrs.

After workup according to general procedure A, the crude product was purified by column chromatography (MPLC, 90 g of silica, flow rate 35 ml/min, $CH_2Cl_2$ with an EtOAc gradient of 1% to 3%) and dried in vacuo. This gave a colorless solid (263 mg, 32% of theory). Mp.: 180° C. (disintegr.), RH: 0.31 (hexane:EtOAc=2:1), $^1$H-NMR (DMSO-$d_6$, 200 MHz): δ=3.76 (s, 3H, $OCH_3$), 3.82 (s, 3H, $OCH_3$), 6.96 (d, $J_3$=8.9 Hz, 2H), 7.10-7.34 (m, 3H), 7.43 (d, $J_3$=8.5 Hz, 1H), 7.53-7.81 (m, 2H), 7.89-8.10 (m, 3H), 10.00 (s, 1H, CHO), 10.45 (s, 1H, NH), $^{13}$C-NMR (DMSO-$d_6$, 50 MHz): δ=52.2 (q, $CO_2\underline{C}H_3$), 55.4 (q, C4'"O$\underline{C}H_3$), 114.4 (d, C3'''+C5'''), 118.9 (s, C4"), 121.3 (d, C2'), 122.6 (d, C2'''+C6'''), 124.1 (d, C4'), 125.1 (d, C6'), 126.2 (d, C6"*), 128.7 (d, C5'), 129.8 (s, C2"), 130.0 (s, C3'), 132.5 (d, C3"*), 138.2 (d, C5"*), 138.6 (s, C1'), 145.2 (s, C1'"), 151.7 (s, C1"), 156.9 (s, C4'"), 165.9 (s, C2*), 166.0 (s, $CO_2$*), 171.5-172.5 (C4+C6, not resolved), 188.4 (d, CHO). MW calcd. for $C_{25}H_{19}BrN_4O_6$: 551.35 g/mol.

Example 17

Preparation of 3-{[4-(4-cyanophenoxy)-6-(4-methoxyphenoxy)-1,3,5-triazin-2-yl]-amino}benzoic acid methyl ester (17)

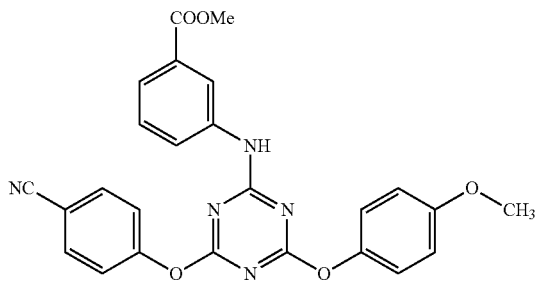

(17)

Preparation was performed according to general procedure A.

Step 1: cyanuric chloride (277 mg, 1.50 mmol), 4-methoxyphenol (186 mg, 1.50 mmol), DIPEA (213 mg, 1.65 mmol); −35° C. for 7 hrs.

Step 2: 5-hydroxybenzonitrile (179 mg, 1.50 mmol), DIPEA (310 mg, 2.40 mmol); 40° C. for 47 hrs.

Step 3: 3-aminobenzoic acid methyl ester (261 mg, 1.73 mmol), DIPEA (291 mg, 2.25 mmol); 40° C. for 23.5 hrs.

After workup according to general procedure A, the crude product was purified by column chromatography (MPLC, silica, flow rate 20 ml/min with pure $CH_2Cl_2$ for 1 hr, followed by 30 ml/min for 20 min, followed by 30 ml/min for 15 min with 2% EtOAc, followed by 40 ml/min with EtOAc) and dried in vacuo. This gave a colorless solid (617 mg, 88% of theory). Mp.: 132-134.5° C. ($CH_2Cl_2$), RH: 0.29 (hexane:EtOAc=2:1), $^1$H-NMR (DMSO-$d_6$, 200 MHz): δ=3.76 (s, 3H, C4'''O$CH_3$), 3.82 (s, 3H, CO$_2CH_3$), 6.96 (d, $J_3$=9.0 Hz, 2H, H3'''+H5'''), 7.17 (d, $J_3$=9 Hz, 2H), 7.28 (t, $J_3$=7.9 Hz, 1H), 7.50 (d, $J_3$=8.6 Hz, 2H), 7.58 (d, $J_3$=7.8 Hz, 1H), 7.63-7.82 (m, 1H), 7.94 (d, $J_3$=8.3 Hz, 2H, H3''+H5''), 8.05 (s, 1H, H2'), 10.47 (s, 1H, NH), $^{13}$C-NMR (DMSO-$d_6$, 50 MHz): δ=52.1 (q, CO$_2$$CH_3$), 55.4 (q, C4'''O$CH_3$), 108.6 (s, C4''), 114.5 (d, C3'''+C5'''), 118.5 (s, CN), 121.3 (d, C2'), 122.6 (d, C2'''+C6'''), 123.2 (d, C2''+C6''), 124.1 (d, C4'), 125.2 (d, C6'), 128.7 (d, C5'), 130.0 (s, C3'), 134.1 (d, C3''+C5''), 138.7 (s, C1'), 145.2 (s, C1'''), 155.2 (s, C1''), 156.9 (s, C4'''), 165.9 (s, C2*), 166.1 (s, CO$_2$*), 171.2+171.6+172.1+172.5 (s, C4+C6, 2 pairs of rotamers). MW calcd. for $C_{25}H_{19}N_5O_5$: 469.45 g/mol.

Example 18

Preparation of 3-[(4.6-diphenoxy-1,3,5-triazin-2-yl)amino]benzoic acid t-butyl ester (18)

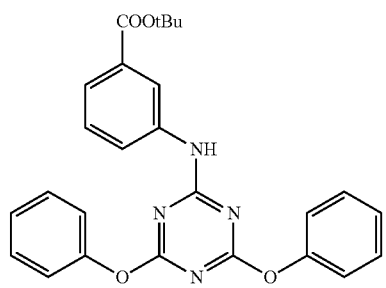

(18)

Preparation was performed according to the general procedure B.

Step 1: cyanuric chloride (92 mg, 0.50 mmol), phenol (47 mg, 0.50 mmol), DIPEA (71 mg, 0.55 mmol); −35° C. for 6 hrs.

Step 2: phenol (47 mg, 0.50 mmol), DIPEA (103 mg, 0.80 mmol); room temperature for 46 hrs.

Step 3: 3-aminobenzoic acid t-butyl ester (111 mg, 0.58 mmol), DIPEA (97 mg, 0.75 mmol); room temperature for 43 hrs.

After workup according to general procedure B1, the crude product was purified by column chromatography (MPLC, silica, flow rate 45 ml/min $CH_2Cl_2$:PE 1:5 with an EtOAc gradient of 1% to 25% over 35 min) and dried in vacuo. This gave colorless crystals (167 mg, 73% of theory). Mp.: 208-209° C. ($CH_2Cl_2$/PE), RH: 0.62 (hexane:EtOAc=2:1), $^1$H-NMR (DMSO-$d_6$, 200 MHz): δ=1.51 (s, 9H, (CH$_3$)$_3$), 7.14-7.34 (m, 7H), 7.39-7.55 (m, 5H), 7.75 (d, $J_3$=8.3 Hz, 1H), 8.02 (s, 1H, H2'), 10.39 (s, 1H, NH), $^{13}$C-NMR (DMSO-$d_6$, 50 MHz): δ=27.7 (q, C($CH_3$)$_3$), 80.6 (s, $C$(CH$_3$)$_3$), 121.3 (d, C2'), 121.8 (d, C2''+C2'''+C6''+C6'''), 123.7 (d, C4'), 124.7 (d, C6'), 125.7 (d, C4''+C4'''), 128.4 (d, C5'), 129.6 (d, C3''+C3'''+C5''+C5'''), 131.7 (s, C3'), 138.7 (s, C1'), 151.8 (s, C1'', C1'''), 164.6 (s, CO$_2$), 166.2 (s, C2), 171.8+172.2 (bs, C4+C6, rotamers). MW calcd. for $C_{26}H_{24}N_4O_4$: 456.49 g/mol.

Example 19

Preparation of 3-{[4-(4-chlorophenoxy)-6-phenoxy-1,3,5-triazin-2-yl]amino}benzoic acid t-butyl ester (19)

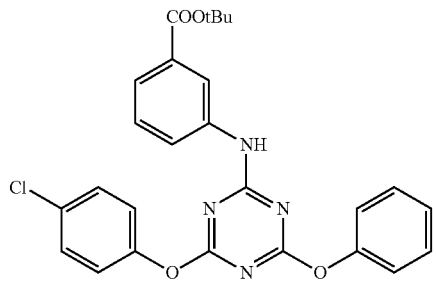

(19)

Preparation was performed according to the general procedure B.

Step 1: cyanuric chloride (92 mg, 0.50 mmol), phenol (47 mg, 0.50 mmol), DIPEA (71 mg, 0.55 mmol); −35° C. for 6 hrs.

Step 2: 4-chlorophenol (64 mg, 0.50 mmol), DIPEA (103 mg, 0.80 mmol); room temperature for 46 hrs.

Step 3: 3-aminobenzoic acid t-butyl ester (111 mg, 0.58 mmol), DIPEA (97 mg, 0.75 mmol); 40° C. for 26 hrs.

After workup according to general procedure B1, the crude product was purified by column chromatography (MPLC, silica, flow rate 45 ml/min $CH_2Cl_2$) and dried in vacuo. This gave a slightly yellowish solid (217 mg, 89% of theory). Mp.: 172.5-174° C. ($CH_2Cl_2$), RH: 0.61 (hexane:EtOAc=2:1), $^1$H-NMR (DMSO-$d_6$, 200 MHz): δ=1.53 (s, 9H, (CH$_3$)$_3$), 7.14-7.37 (m, 6H), 7.39-7.58 (m, 5H), 7.73 (d, $J_3$=8.1 Hz, 1H), 8.04 (s, 1H, H2'), 10.42 (s, 1H, NH), $^{13}$C-NMR (DMSO-$d_6$, 50 MHz): δ=27.8 (q, C($CH_3$)$_3$), 80.7 (s, $C$(CH$_3$)$_3$), 121.3 (d, C2'), 121.8 (d, C2'''+C6'''), 123.77 (d, C2''+C6''), 123.85 (d, C4'), 124.8 (d, C6'), 125.7 (d, C4'''), 128.4 (d, C5'), 129.4 (d, C3''*+C5''*), 129.6 (d, C3'''*+C5'''*), 129.9 (s, C4''), 131.7 (s, C3'), 138.6 (s, C1'), 150.6

(s, C1''), 151.8 (s, C1'''), 164.6 (s, CO$_2$), 166.1 (s, C2), 171.5-172.4 (C4+C6, not resolved). MW calcd. for C$_{26}$H$_{23}$ClN$_4$O$_4$: 490.94 g/mol.

Example 20

Preparation of 3-{[4-(3-chlorophenoxy)-6-phenoxy-1,3,5-triazin-2-yl]amino}benzoic acid t-butyl ester (20)

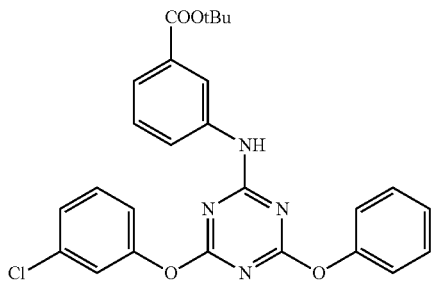

(20)

Preparation was performed according to the general procedure B.

Step 1: cyanuric chloride (92 mg, 0.50 mmol), phenol (47 mg, 0.50 mmol), DIPEA (71 mg, 0.55 mmol); −35° C. for 6 hrs.

Step 2: 3-chlorophenol (64 mg, 0.50 mmol), DIPEA (103 mg, 0.80 mmol); room temperature for 46 hrs.

Step 3: 3-aminobenzoic acid t-butyl ester (111 mg, 0.58 mmol), DIPEA (97 mg, 0.75 mmol); 40° C. for 26 hrs.

After workup according to general procedure B1, the crude product was purified by column chromatography (MPLC, silica, flow rate 45 ml/min PE/CH$_2$Cl$_2$/EtOAC=10:2:1, 2% Et$_3$N) and dried in vacuo. This gave a colorless solid (186 mg, 76% of theory). Mp.: 187.5-190.5° C. (PE/CH$_2$Cl$_2$/EtOAc), RH: 0.64 (hexane:EtOAc=2:1), $^1$H-NMR (DMSO-d$_6$, 200 MHz): δ=1.52 (s, 9H, (CH$_3$)$_3$), 7.13-7.60 (m, 11H), 7.77 (d, J$_3$=8.0 Hz, 1H), 8.04 (s, 1H, H2'), 10.45 (s, 1H, NH), $^{13}$C-NMR (DMSO-d$_6$, 50 MHz): δ=27.7 (q, C(CH$_3$)$_3$), 80.6 (s, C(CH$_3$)$_3$), 120.7 (d, C6''), 121.3 (d, C2'), 121.7 (d, C2'''+C6'''), 122.3 (d, C2''), 123.8 (d, C4'), 124.7 (d, C6'), 125.6 (d, C4'''), 125.8 (d, C4''), 128.4 (d, C5'), 129.5 (d, C3'''+C5'''), 130.8 (d, C5''), 131.7 (s, C3'), 133.4 (s, C3''), 138.6 (s, C1'), 151.8 (s, C1'''), 152.4 (s, C1''), 164.5 (s, CO$_2$*), 166.1 (s, C2), 171.2-172.2 (C4+C6, not resolved). MW calcd. for C$_{26}$H$_{23}$ClN$_4$O$_4$: 490.94 g/mol.

Example 21

Preparation of 3-{[4-(2-chlorophenoxy)-6-phenoxy-1,3,5-triazin-2-yl]amino}benzoic acid t-butyl ester (21)

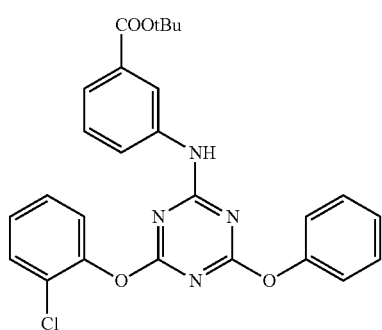

(21)

Preparation was performed according to the general procedure B.

Step 1: cyanuric chloride (92 mg, 0.50 mmol), phenol (47 mg, 0.50 mmol), DIPEA (71 mg, 0.55 mmol); −35° C. for 6 hrs.

Step 2: 2-chlorophenol (64 mg, 0.50 mmol), DIPEA (103 mg, 0.80 mmol); room temperature for 46 hrs.

Step 3: 3-aminobenzoic acid t-butyl ester (111 mg, 0.58 mmol), DIPEA (97 mg, 0.75 mmol); 40° C. for 26 hrs.

After workup according to general procedure B1, the crude product was purified by column chromatography (MPLC, silica, flow rate 45 ml/min PE/CH$_2$Cl$_2$/EtOAC=80:8:1, 2% Et$_3$N) and dried in vacuo, This gave colorless crystals (189 mg, 77% of theory). Mp.: 191-192° C. (PE/CH$_2$Cl$_2$/EtOAc), RH: 0.63 (hexane:EtOAc=2:1), $^1$H-NMR (DMSO-d$_6$, 200 MHz): δ=1.52 (s, 9H, (CH$_3$)$_3$), 7.11-7.56 (m, 10H), 756-7.79 (m, 2H), 7.99 (s, 1H, H2'), 10.48 (s, 1H, NH), $^{13}$C-NMR (DMSO-d$_6$, 50 MHz): δ=27.7 (q, C(CH$_3$)$_3$), 80.6 (s, C(CH$_3$)$_3$), 121.3 (d, C2'), 121.7 (d, C2'''+C6'''), 123.8 (d, C4'), 124.2 (d, C6''), 124.7 (d, C6'), 125.7 (d, C4'''), 125.9 (s, C2''), 127.4 (d, C4''*), 128.4 (d, C5''*), 128.5 (d, C5'*), 129.5 (d, C3'''+C5'''), 130.2 (d, C3''), 131.6 (s, C3'), 138.4 (s, C1'), 147.7 (s, C1''), 151.7 (s, C1'''), 164.5 (s, CO$_2$), 166.1 (s, C2), 171.2+171.6+171.8+172.2 (C4+C6, 2 pairs of rotamers). MW calcd. for C$_{26}$H$_{23}$ClN$_4$O$_4$: 490.94 g/mol.

Example 22

Preparation of 3-{[4-(4-t-butylphenoxy)-6-phenoxy-1,3,5-triazin-2-yl]amino}benzoic acid t-butyl ester (22)

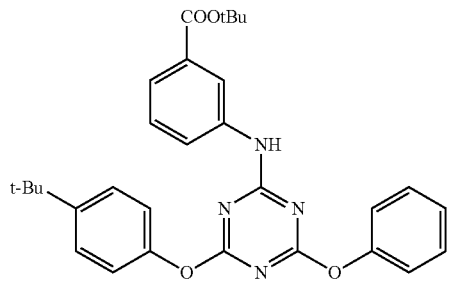

(22)

Preparation was performed according to the general procedure B.

Step 1: cyanuric chloride (92 mg, 0.50 mmol), phenol (47 mg, 0.50 mmol), DIPEA (71 mg, 0.55 mmol); −35° C. for 7 hrs.

Step 2: 4-t-butyl phenol (75 mg, 0.50 mmol), DIPEA (103 mg, 0.80 mmol); 40° C. for 47 hrs.

Step 3: 3-aminobenzoic acid t-butyl ester (111 mg, 0.58 mmol), DIPEA (97 mg, 0.75 mmol); 40° C. for 43 hrs.

After workup according to general procedure B1, the crude product was purified by column chromatography (MPLC, silica, flow rate 45 ml/min PE/CH$_2$Cl$_2$=5:1, with an EtOAc gradient of 1% to 25% over 35 min) and dried in vacuo. This gave a colorless solid (170 mg, 67% of theory). Mp.: 139-141° C. (PE/CH$_2$Cl$_2$), RH: 0.75 (hexane:EtOAc=2:1), $^1$H-NMR (DMSO-d$_6$, 200 MHz): δ=1.31 (s, 9H, C4''C(CH$_3$)$_3$), 1.52 (s, 9H, CO$_2$C(CH$_3$)$_3$), 7.10-7.35 (m, 6H), 7.37-7.58 (m, 5H), 7.78 (d, J$_3$=7.3 Hz, 1H), 8.03 (s, 1H, H2'), 10.39 (s, 1H, NH), $^{13}$C-NMR (DMSO-d$_6$, 50 MHz): δ=27.8 (q, CO$_2$C(CH$_3$)$_3$), 31.3 (q, C4''C(CH$_3$)$_3$), 34.3 (s, C4″C(CH₃)₃), 80.7 (s, CO₂C(CH₃)₃), 121.2 (d, C2″+C6″*), 121.3 (d, C2′*), 121.8 (d, C2‴+C6‴), 123.7 (d, C4′), 124.7 (d, C6′), 125.7 (d, C4‴), 126.2 (d, C3″+C5″), 128.4 (d, C5′), 129.6 (d, C3‴+C5‴), 131.6 (s, C3′), 138.7 (s, C1′), 148.0 (s, C4″*), 149.5 (s, C1′*), 151.8 (s, C1‴), 164.6 (s, CO₂), 166.2 (s, C2), 171.4-172.3 (C4+C6, not resolved). MW calcd. for $C_{30}H_{32}N_4O_4$: 512.60 g/mol.

Example 23

Preparation of 3-{[4-(4-methoxyphenoxy)-6-phenoxy-1,3,5-triazin-2-yl]amino}benzoic acid t-butyl ester (23)

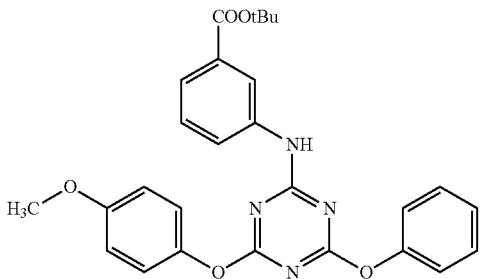 [SMILES: COC(=O)c1cccc(Nc2nc(Oc3ccccc3)nc(Oc3ccc(OC)cc3)n2)c1]

(23)

Preparation was performed according to the general procedure B.

Step 1: cyanuric chloride (92 mg, 0.50 mmol), phenol (47 mg, 0.50 mmol), DIPEA (71 mg, 0.55 mmol); −35° C. for 7 hrs.

Step 2: 4-methoxyphenol (62 mg, 0.50 mmol), DIPEA (103 mg, 0.80 mmol); 40° C. for 47 hrs.

Step 3: 3-aminobenzoic acid t-butyl ester (111 mg, 0.58 mmol), DIPEA (97 mg, 0.75 mmol); 40° C. for 43 hrs.

After workup according to general procedure B2, Et₂O (2 ml) and PE (3 ml) were added, and the oily material was sonicated for induction of precipitation. PE (10 ml) was added to the supernatant in order to induce crystallization of a second fraction that was separated off by centrifugation. The combined fractions were purified by column chromatography (MPLC, silica, flow rate: 45 ml/min, PE with an Et₂O gradient of 15% to 75% over 80 min) and dried in vacuo. This gave colorless crystals (167 mg, 68% of theory). Mp.: 68-70° C. (PE/Et₂O), RH: 0.56 (hexane:EtOAc=2:1), ¹H-NMR (DMSO-d₆, 200 MHz): δ=1.52 (s, 9H, (CH₃)₃), 3.77 (s, 3H, OCH₃), 6.97 (d, J₃=9.1 Hz, 2H, H3″+H5″), 7.12-7.34 (m, 6H), 7.38-7.58 (m, 3H), 7.77 (d, J₃=7.5 Hz, 1H), 8.04 (s, 1H, H2′), 10.37 (s, 1H, NH), ¹³C-NMR (DMSO-d₆, 50 MHz): δ=27.8 (q, C(CH₃)₃), 55.5 (q, OCH₃), 80.7 (s, C(CH₃)₃), 114.5 (d, C3″+C5″), 121.2 (d, C2′), 121.8 (d, C2‴+C6‴), 122.6 (d, C2″+C6″), 123.8 (d, C4′), 124.8 (d, C6′), 125.7 (d, C4‴), 128.5 (d, C5′), 129.6 (d, C3‴+C5‴), 131.7 (s, C3′), 138.7 (s, C1′), 145.2 (s, C1″), 151.8 (s, C1‴), 156.9 (s, C4″), 164.6 (s, CO₂), 166.2 (s, C2), 171.2-172.4 (C4+C6, not resolved). MW calcd. for $C_{27}H_{26}N_4O_6$: 486.52 g/mol.

Example 24

Preparation of 3-{[4-(4-cyanophenoxy)-6-phenoxy-1,3,5-triazin-2-yl]amino}benzoic acid t-butyl ester (24)

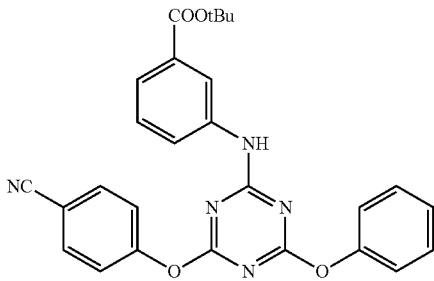 [SMILES: COC(=O)c1cccc(Nc2nc(Oc3ccccc3)nc(Oc3ccc(C#N)cc3)n2)c1]

(24)

Preparation was performed according to the general procedure B.

Step 1: cyanuric chloride (92 mg, 0.50 mmol), phenol (47 mg, 0.50 mmol), DIPEA (71 mg, 0.55 mmol); −35° C. for 7 hrs.

Step 2: 4-hydroxybenzonitrile (60 mg, 0.50 mmol), DIPEA (103 mg, 0.80 mmol); 40° C. for 47 hrs.

Step 3: 3-aminobenzoic acid t-butyl ester (111 mg, 0.58 mmol), DIPEA (97 mg, 0.75 mmol); 40° C. for 43 hrs.

After workup according to general procedure B2, the crude product was purified by column chromatography (MPLC, silica, flow rate: 45 ml/min, applied with CH₂Cl₂, eluted with PE having an EtOAc gradient of 4% to 76% over 80 min) and dried in vacuo. This gave a colorless solid (81 mg, 33% of theory). Mp.: 176.5-178.5° C. (PE/EtOAc), RH: 0.49 (hexane:EtOAc=2:1), ¹H-NMR (DMSO-d₆, 200 MHz): δ=1.53 (s, 9H, (CH₃)₃), 7.17-7.34 (m, 4H), 7.38-7.58 (m, 5H), 7.71 (bs, 1H), 7.94 (d, J₃=8.5 Hz, 2H, H3″+H5″), 8.04 (s, 1H, H2′), 10.46 (s, 1H, NH), ¹³C-NMR (DMSO-d₆, 50 MHz): δ=27.8 (q, C(CH₃)₃), 80.7 (s, C(CH₃)₃), 108.5 (s, C4″), 118.5 (s, CN), 121.3 (d, C2′), 121.8 (d, C2‴+C6‴), 123.2 (d, C2″+C6″), 123.9 (d, C4′*), 124.1 (d, C6′*), 125.8 (d, C4‴), 128.5 (d, C5′), 129.6 (d, C3‴+C5‴), 131.7 (s, C3′), 134.1 (d, C3″+C5″), 138.5 (s, C1′), 151.7 (s, C1‴), 155.2 (s, C1″), 164.5 (s, CO₂), 166.2 (s, C2); C4+C6 not visible. MW calcd. for $C_{27}H_{23}N_5O_4$: 481.50 g/mol.

Example 25

Preparation of 3-{[4-(3-nitrophenoxy)-6-phenoxy-1,3,5-triazin-2-yl]amino}benzoic acid t-butyl ester (25)

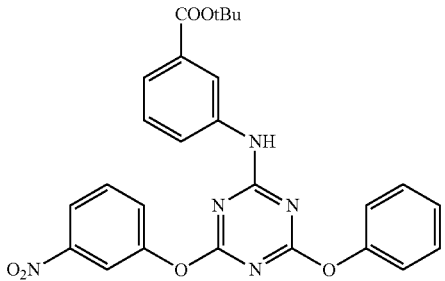 [SMILES: COC(=O)c1cccc(Nc2nc(Oc3ccccc3)nc(Oc3cccc([N+](=O)[O-])c3)n2)c1]

(25)

Preparation was performed according to the general procedure B.

Step 1: cyanuric chloride (92 mg, 0.50 mmol), phenol (47 mg, 0.50 mmol), DIPEA (71 mg, 0.55 mmol); −35° C. for 7 hrs.

Step 2: 3-nitrophenol (70 mg, 0.50 mmol), DIPEA (103 mg, 0.80 mmol); 40° C. for 47 hrs.

Step 3: 3-aminobenzoic acid t-butyl ester (111 mg, 0.58 mmol), DIPEA (97 mg, 0.75 mmol); 40° C. for 43 hrs.

After workup according to general procedure B2, EtOAc (1 ml) and PE (9 ml) were added, and the oily material was sonicated for induction of precipitation, The supernatant was separated, and the crude product was purified by preparative thin-layer chromatography (PE:EtOAc=3:1) and dried in vacuo, This gave a yellowish solid (83 mg, 33% of theory). Mp.: 137-148° C. (PE/EtOAc), RH: 0.47 (hexane:EtOAc=2:1), $^1$H-NMR (DMSO-$d_6$, 200 MHz): δ=1.51 (s, 9H, $(CH_3)_3$), 7.16-7.32 (m, 4H), 7.35-7.57 (m, 3H), 7.62-7.84 (m, 3H), 8.04 (s, 1H, H2'), 8.15 (dt, $J_3$=7.2 Hz, $J_4$=2.0 Hz, 1H), 8.22 (s, 1H, H2''), 10.48 (s, 1H, NH), $^{13}$C-NMR (DMSO-$d_6$, 50 MHz): δ=27.7 (q, C($\underline{C}H_3)_3$), 80.7 (s, $\underline{C}(CH_3)_3$), 117.4 (d, C2''), 120.7 (d, C2'), 121.2 (d, C4''), 121.7 (d, C2'''+C6'''), 124.0 (d, C4'), 124.8 (d, C6'), 125.7 (d, C4'''), 128.5 (d, C6''*), 128.8 (d, C5'*), 129.6 (d, C3'''+C5'''), 130.8 (d, C5''), 131.7 (s, C3'), 138.5 (s, C1'), 148.4 (s, C3''), 151.7 (s, C1'''*), 152.0 (s, C1''*), 164.5 (s, $CO_2$), 166.1 (s, C2); C4+C6 not visible. MW calcd. for $C_{26}H_{23}N_5O_6$: 490.94 g/mol.

Example 26

Preparation of 3-{[4-(4-formyl-2-methoxyphenoxy)-6-phenoxy-1,3,5-triazin-2-yl]-amino}benzoic acid t-butyl ester (26)

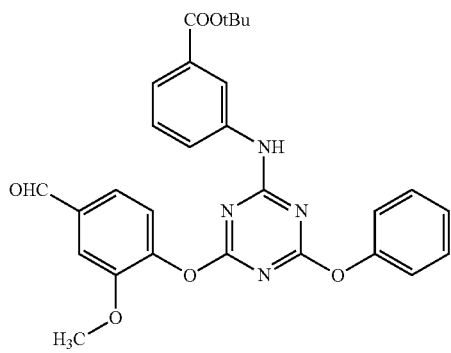

(26)

Preparation was performed according to the general procedure B.

Step 1: cyanuric chloride (92 mg, 0.50 mmol), phenol (47 mg, 0.50 mmol), DIPEA (71 mg, 0.55 mmol); −35° C. for 7 hrs.

Step 2: 4-hydroxy-3-methoxybenzaldehyde (76 mg, 0.50 mmol), DIPEA (103 mg, 0.80 mmol); 40° C. for 47 hrs.

Step 3: 3-aminobenzoic acid t-butyl ester (111 mg, 0.58 mmol), DIPEA (97 mg, 0.75 mmol); 40° C. for 43 hrs.

After workup according to general procedure B2, the crude product was purified by column chromatography (MPLC, silica gel, flow rate: 45 ml/min, PE with an EtOAc gradient of 1% to 40% over 1 h) and dried in vacuo. This gave a colorless solid (141 mg, 55% of theory). Mp.: 76-79° C. (PE/EtOAc), RH: 0.31 (hexane:EtOAc=2:1), $^1$H-NMR (DMSO-$d_6$, 200 MHz): δ=1.51 (s, 9H, $(CH_3)_3$), 3.86 (s, 3H, $OCH_3$), 7.11-7.33 (m, 4H), 7.36-7.55 (m, 4H), 7.56-7.78 (m, 3H), 8.00 (s, 1H, H2'), 10.00 (s, 1H, CHO), 10.43 (s, 1H, NH), $^{13}$C-NMR (DMSO-$d_6$, 50 MHz): δ=27.8 (q, C($\underline{C}H_3)_3$), 56.2 (q, $OCH_3$), 80.8 (s, $\underline{C}(CH_3)_3$), 112.3 (d, C3''), 121.3 (d, C2'), 121.8 (d, C2'''+C6'''), 123.6 (d, C5''*), 123.8 (d, C4'*), 123.9 (d, C6''*), 124.7 (d, C6'), 125.8 (d, C4'''), 128.5 (d, C5'), 129.6 (d, C3'''+C5'''), 131.7 (s, C3'), 135.1 (s, C4''), 138.6 (s, C1'), 145.3 (s, C1''*), 151.70 (s, C2''*) 151.74 (s, C1'''*), 164.6 (s, $CO_2$), 166.1 (s, C2), 192.2 (d, CHO); C4+C6 not visible. MW calcd. for $C_{28}H_{26}N_4O_6$: 514.53 g/mol.

Example 27

Preparation of 3-{[4-(4-formyl-2-methoxyphenoxy)-6-(4-methoxyphenoxy)-1,3,5-triazin-2-yl] amino}benzoic acid t-butyl ester (27)

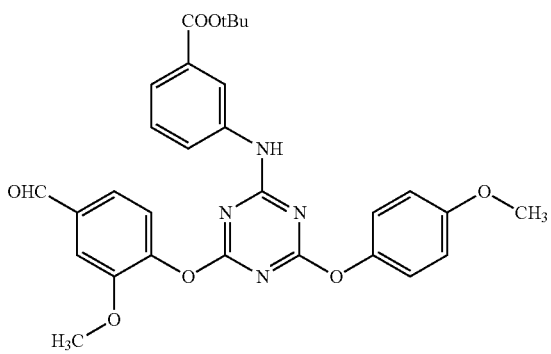

(27)

Preparation was performed according to the general procedure B.

Step 1: cyanuric chloride (92 mg, 0.50 mmol), 4-methoxyphenol (62 mg, 0.50 mmol), DIPEA (71 mg, 0.55 mmol); −35° C. for 6 hrs.

Step 2: 4-hydroxy-3-methoxybenzaldehyde (76 mg, 0.50 mmol), DIPEA (103 mg, 0.80 mmol); 40° C. for 45 hrs.

Step 3: 3-aminobenzoic acid t-butyl ester (111 mg, 0.58 mmol), DIPEA (97 mg, 0.75 mmol); 40° C. for 22 hrs.

After workup according to general procedure B2, the crude product was purified by column chromatography (MPLC, silica gel, flow rate: 50 ml/min, PE with an EtOAc gradient of 20% to 40% over 30 min) and dried in vacuo, This gave a colorless solid (162 mg, 59% of theory). Mp.: 88-106° C. (PE/EtOAc), RH: 0.30 (hexane:EtOAc=2:1), $^1$H-NMR (DMSO-$d_6$, 200 MHz): δ=1.52 (s, 9H, $(CH_3)_3$), 3.76 (s, 3H, C4'''$OCH_3$), 3.86 (s, 3H, C2''$OCH_3$), 6.96 (d, $J_3$=9.0 Hz, 2H, H3'''+H5'''), 7.10-7.31 (m, 3H), 7.44-7.86 (m, 5H), 8.02 (s, 1H, H2'), 10.01 (s, 1H, CHO), 10.42 (s, 1H, NH), $^{13}$C-NMR (DMSO-$d_6$, 50 MHz): δ=27.7 (q, C($\underline{C}H_3)_3$), 55.4 (q, C4'''O$\underline{C}H_3$), 56.1 (q, C2''O$\underline{C}H_3$), 80.7 (s, $\underline{C}(CH_3)_3$), 112.2 (d, C3''), 114.5 (d, C3'''+C5'''), 121.2 (d, C2'), 122.6 (d, C2''+C6'''), 123.6 (d, C5''*), 123.8 (d, C4'*), 123.9 (d, C6''*), 124.6 (d, C6'), 128.5 (d, C5'), 131.7 (s, C3'), 135.0 (s, C4''), 138.6 (s, C1'), 145.2 (s, C1''*), 145.3 (s, C1'''*), 151.8 (s, C2''), 156.9 (s, C4'''), 164.6 (s, $CO_2$), 166.1 (s, C2), 192.1 (d, CHO); C4+C6 not visible. MW calcd. for $C_{29}H_{28}N_4O_7$: 544.56 g/mol.

Example 28

Preparation of 3-{[4-(4-cyanophenoxy)-6-(4-methoxyphenoxy)-1,3,5-triazin-2-yl]-amino}benzoic acid t-butyl ester (28)

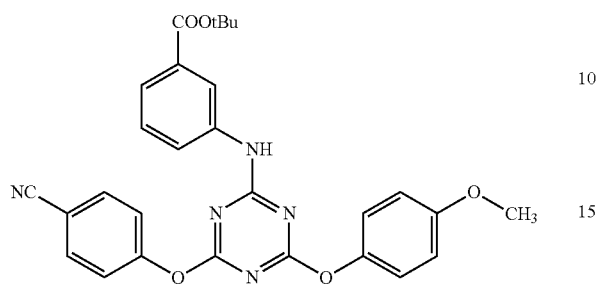
(28)

Preparation was performed according to the general procedure B.

Step 1: cyanuric chloride (92 mg, 0.50 mmol), 4-methoxyphenol (62 mg, 0.50 mmol), DIPEA (71 mg, 0.55 mmol); −35° C. for 7 hrs.

Step 2: 4-hydroxybenzonitrile (60 mg, 0.50 mmol), DIPEA (103 mg, 0.80 mmol); 40° C. for 47 hrs.

Step 3: 3-aminobenzoic acid t-butyl ester (111 mg, 0.58 mmol), DIPEA (97 mg, 0.75 mmol); 40° C. for 43 hrs.

After workup according to general procedure B2, the crude product was purified by column chromatography (MPLC, silica gel, flow rate: 45 ml/min, PE with an EtOAc gradient of 10% to 40% over 1 hr) and dried in vacuo. This gave a colorless solid (145 mg, 57% of theory). Mp.: 161-164° C. (PE/EtOAc), RH: 0.43 (hexane:EtOAc=2:1), $^1$H-NMR (DMSO-$d_6$, 200 MHz): δ=1.53 (s, 9H, (CH$_3$)$_3$), 3.77 (s, 3H, OCH$_3$), 6.98 (d, $J_3$=9.0 Hz, 2H, H3'''+H5'''), 7.11-7.32 (m, 3H), 7.46-7.59 (m, 3H), 7.61-7.84 (m, 1H), 7.94 (d, $J_3$=8.4 Hz, 2H, H3''+H5''), 8.05 (s, 1H, H2'), 10.45 (s, 1H, NH), $^{13}$C-NMR (DMSO-$d_6$, 50 MHz): δ=27.8 (q, C(CH$_3$)$_3$), 55.6 (q, C4'''OCH$_3$), 80.8 (s, C(CH$_3$)$_3$), 108.5 (s, C4''), 114.5 (d, C3'''+C5'''), 118.4 (s, CN), 121.3 (d, C2'), 122.6 (d, C2''+C6'''), 123.2 (d, C2''+C6''), 124.0 (d, C4'), 124.9 (d, C6'), 128.5 (d, C5'), 131.7 (s, C3'), 134.1 (d, C3''+C5''), 138.6 (s, C1'), 145.2 (s, C1'''), 155.2 (s, C1''), 156.9 (s, C4'''), 164.6 (s, CO$_2$), 166.1 (s, C2); C4+C6 not visible. MW calcd. for C$_{28}$H$_{25}$N$_5$O$_5$: 511.53 g/mol.

Example 29

Preparation of 3-{[4-(4-chlorophenoxy)-6-phenoxy-1,3,5-triazin-2-yl]amino}benzoic acid (29)

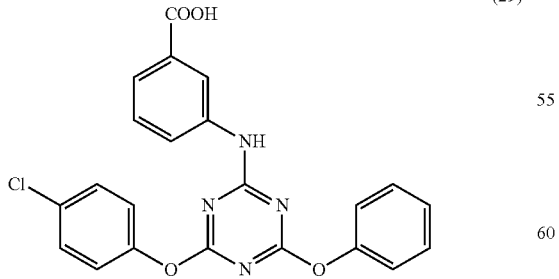
(29)

Preparation was performed according to the above general procedure C from 3-{[4-(4-chlorophenoxy)-6-phenoxy-1,3,5-triazin-2-yl]amino}benzoic acid-t-butylester (22) (49 mg, 0.10 mmol) obtained in example 19 at 50° C. for 1 hr, which gave a beige solid (44 mg, quantitative). Mp.: 244-247° C. (Et$_2$O), RH: 0.63 (hexane:EtOH=1:1), $^1$H-NMR (DMSO-$d_6$, 200 MHz): δ=7.14-7.38 (m, 6H), 7.38-7.63 (m, 5H), 7.72 (d, $J_3$=8.4 Hz, 1H), 8.04 (s, 1H, H2'), 10.42 (s, 1H, NH), 12.91 (bs, 1H, CO$_2$H), $^{13}$C-NMR (DMSO-$d_6$, 50 MHz): δ=121.5 (d, C2'), 121.8 (d, C2'''+C6'''), 123.8 (d, C2''+C6''), 124.2 (d, C4'), 124.8 (d, C6'), 125.8 (d, C4'''), 128.5 (d, C5'), 129-5 (d, C3''*+C5''*), 129.6 (d, C3'''*+C5'''*), 129.9 (s, C4''), 131.2 (s, C3'), 138.5 (s, C1'), 150.6 (s, C1''), 151.8 (s, C1'''), 166.1 (s, C2), 167.0 (s, CO$_2$), 171.3-172.4 (C4+C6). MW calcd. for C$_{22}$H$_{15}$ClN$_4$O$_4$: 434.83 g/mol.

Example 30

Preparation of 3-{[4-(3-chlorophenoxy)-6-phenoxy-1,3,5-triazin-2-yl]amino}benzoic acid (30)

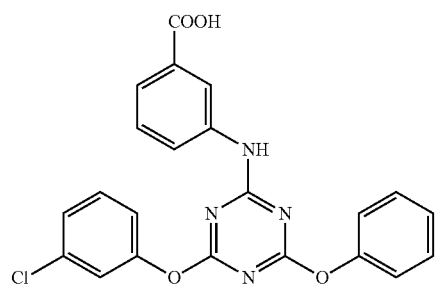
(30)

Preparation was performed according to the above general procedure C from 3-{[4-(3-chlorophenoxy)-6-phenoxy-1,3,5-triazin-2-yl]amino}benzoic acid-t-butylester (23) (49 mg, 0.10 mmol) obtained in example 20 at 50° C. for 1 hr, which gave a slightly yellowish solid (44 g, quantitative). Mp.: 227-230° C. (Et$_2$O), RH: 0.59 (hexane:EtOH=1:1), $^1$H-NMR (DMSO-$d_6$, 200 MHz): δ=7.16-7.53 (m, 10H), 7.58 (d, $J_3$=7.7 Hz, 1H), 7.75 (d, $J_3$=7.9 Hz, 1H), 8.04 (s, 1H, H2'), 10.45 (s, 1H, NH), 12.97 (bs, 1H, CO$_2$H), $^{13}$C-NMR (DMSO-$d_6$, 50 MHz): δ=120.8 (d, C6''), 121.5 (d, C2'), 121.8 (d, C2'''+C6'''), 122.4 (d, C2''), 124.3 (d, C4'), 124.8 (d, C6'), 125.8 (d, C4'''), 125.9 (d, C4''), 128.5 (d, C5'), 129.6 (d, C3'''+C5'''), 131.0 (d, C5''), 131.4 (s, C3'), 133.4 (s, C3''), 138.5 (s, C1'), 151.8 (s, C1'''), 152.4 (s, C1''), 166.2 (s, C2), 167.1 (s, CO$_2$*), 171.3-172.3 (C4+C6, not resolved). MW calcd. for C$_{22}$H$_{15}$ClN$_4$O$_4$: 434.83 g/mol.

Example 31

Preparation of 3-{[4-(2-chlorophenoxy)-6-phenoxy-1,3,5-triazin-2-yl]amino}benzoic acid (31)

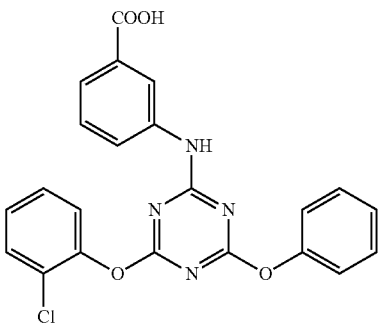 [SMILES: O=C(O)c1cccc(Nc2nc(Oc3ccccc3)nc(Oc3ccccc3Cl)n2)c1]
(31)

Preparation was performed according to the above general procedure C from 3-{[4-(3-chlorophenoxy)-6-phenoxy-1,3,5-triazin-2-yl]amino}benzoic acid t-butyl ester (24) (49 mg, 0.10 mmol) obtained in example 21 at 50° C. for 1 hr, which gave colorless crystals (44 g, quantitative). Mp.: 249.5-251.5° C. (Et$_2$O), RH: 0.60 (hexane:EtOH=1:1), $^1$H-NMR (DMSO-d$_6$, 200 MHz): δ=7.13-7.51 (m, 9H), 7.52-7.75 (m, 3H), 7.99 (s, 1H, H2'), 10.49 (s, 1H, NH), 12.93 (bs, 1H, CO$_2$H), $^{13}$C-NMR (DMSO-d$_6$, 50 MHz): δ=121.6 (d, C2'), 121.8 (d, C2'''+C6'''), 124.3 (d, C6''*), 124.8 (d, C6'), 125.8 (d, C4'''), 126.0 (s, C2''), 127.5 (d, C4''*), 128.5 (d, C5''*), 128.6 (d, C5'*), 129.7 (d, C3'''+C5'''), 130.3 (d, C3''), 131.3 (s, C3'), 138.5 (s, C1'), 147.7 (s, C1''), 151.8 (s, C1'''), 166.2 (s, C2), 167.1 (s, CO$_2$), 171.2-172.5 (C4+C6, not resolved); one d signal was missing, probably due to overlapping. MW calcd. for C$_{22}$H$_{15}$ClN$_4$O$_4$: 434.83 g/mol.

Example 32

Preparation of 3-{[4-(4-t-butylphenoxy)-6-phenoxy-1,3,5-triazin-2-yl]amino}benzoic acid (32)

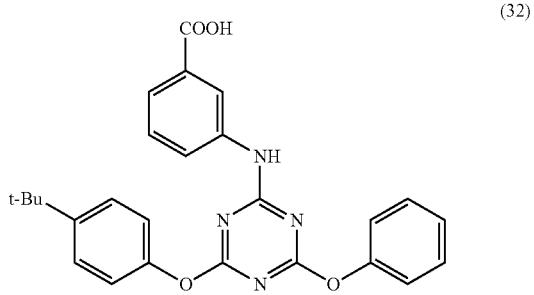

(32)

Preparation was performed according to the above general procedure C from 3-{[4-(4-t-butylphenoxy)-6-phenoxy-1,3,5-triazin-2-yl]amino}benzoic acid t-butyl ester (25) (51 mg, 0.10 mmol) obtained in example 22 at 45° C. for 1 hr, which gave a slightly yellowish solid (46 mg, quantitative). Mp.: 245-247° C. (Et$_2$O), RH: 0.67 (hexane:EtOH=1:1), $^1$H-NMR (DMSO-d$_6$, 200 MHz): δ=1.30 (s, 9H, (CH$_3$)$_3$), 7.10-7.33 (m, 6H), 7.37-7.51 (m, 4H), 7.57 (d, J$_3$=7.7 Hz, 1H), 7.75 (d, J$_3$=8.7 Hz, 1H), 8.05 (s, 1H, H2'), 10.40 (s, 1H, NH), 12.92 (bs, 1H, CO$_2$H), $^{13}$C-NMR (DMSO-d$_6$, 50 MHz): δ=31.3 (q, C(CH$_3$)$_3$), 34.3 (s, C(CH$_3$)$_3$), 121.2 (d, C2''+C6''), 121.6 (d, C2'), 121.8 (d, C2'''+C6'''), 124.1 (d, C4'), 124.8 (d, C6'), 125.7 (d, C4'''), 126.3 (d, C3'''+C5'''), 128.4 (d, C5'), 129.6 (d, C3'''+C5'''), 131.2 (s, C3'), 138.7 (s, C1'), 148.0 (s, C4''*), 149.5 (s, C1''*), 151.8 (s, C1'''), 166.2 (s, C2), 167.1 (s, CO$_2$), 171.6-172.7 (C4+C6, not resolved). MW calcd. for C$_{26}$H$_{24}$N$_4$O$_4$: 456.49 g/mol.

Example 33

Preparation of 3-{[4-(4-methoxyphenoxy)-6-phenoxy-1,3,5-triazin-2-yl]amino}benzoic acid (33)

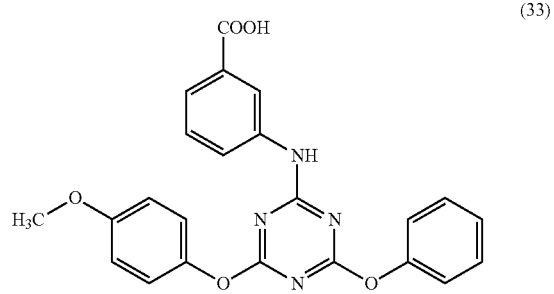

(33)

Preparation was performed according to the above general procedure C from 3-{[4-(4-methoxyphenoxy)-6-phenoxy-1, 3,5-triazin-2-yl]amino}benzoic acid t-butyl ester (26) (49 mg, 0.10 mmol) obtained in example 23 at 50° C. for 1 hr, which gave a slightly yellowish solid (43 mg, quantitative). Mp.: 233-236.5° C. (Et$_2$O), RH: 0.65 (hexane:EtOH=1:1), $^1$H-NMR (DMSO-d$_6$, 200 MHz): δ=3.77 (s, 3H, OCH$_3$), 6.97 (d, J$_3$=9.0 Hz, 2H, H3''+H5''), 7.13-7.34 (m, 6H), 7.39-7.51 (m, 2H), 7.56 (d, J$_3$=7.6 Hz, 1H), 7.74 (d, J$_3$=8.2 Hz, 1H), 8.04 (s, 1H, H2'), 10.37 (s, 1H, NH), 12.93 (bs, 1H, CO$_2$H), $^{13}$C-NMR (DMSO-d$_6$, 50 MHz): δ=55.5 (q, OCH$_3$), 114.5 (d, C3''+C5''), 121.5 (d, C2'), 121.8 (d, C2'''+C6'''), 122.7 (d, C2''+C6''), 124.1 (d, C4'), 124.8 (d, C6'), 125.7 (d, C4'''), 128.5 (d, C5'), 129.6 (d, C3'''+C5'''), 131.3 (s, C3'), 138.6 (s, C1'), 145.2 (s, C1''), 151.8 (s, C1'''), 156.9 (s, C4''), 166.2 (s, C2), 167.1 (s, CO$_2$), 171.3-172.7 (C4+C6, not resolved). MW calcd. for C$_{23}$H$_{18}$N$_4$O$_5$: 430.41 g/mol.

Example 34

Preparation of 3-{[4-(4-cyanophenoxy)-6-phenoxy-1,3,5-triazin-2-yl]amino}benzoic acid (34)

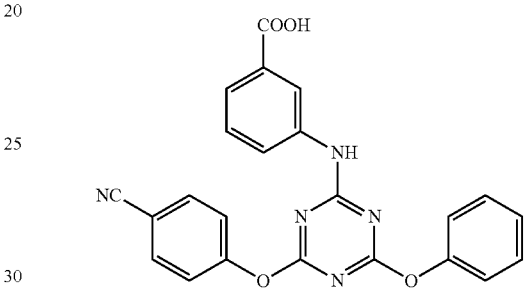

(34)

Preparation was performed according to the above general procedure C from 3-{[4-(4-cyanophenoxy)-6-phenoxy-1,3,5-triazin-2-yl]amino}benzoic acid t-butyl ester (27) (48 mg, 0.10 mmol) obtained in example 24 at 45° C. for 1 hr, which gave a colorless solid (43 mg, quantitative). Mp.: 150° C. (distintegr.), RH: 0.65 (hexane:EtOH=1:1), $^1$H-NMR (DMSO-d$_6$, 200 MHz): δ=7.16-7.35 (m, 4H), 7.37-7.77 (m, 6H), 7.94 (d, J$_3$=8.1 Hz, 2H, H3''+H5''), 8.06 (s, 1H, H2'), 10.48 (s, 1H, NH); CO$_2$H not visible, $^{13}$C-NMR (DMSO-d$_6$, 50 MHz): δ=108.6 (s, C4''), 118.5 (s, CN), 121.66 (d, C2'), 121.76 (d, C2'''+C6'''), 123.3 (d, C2''+C6''), 124.4 (d, C4'), 124.8 (d, C6'), 125.8 (d, C4'''), 128.5 (d, C5'), 129.6 (d, C3'''+C5'''), 131.6 (s, C3'), 134.0 (d, C3''+C5''), 138.4 (s, C1'), 151.6 (s, C1'''), 155.2 (s, C1''), 166.2 (s, C2), 167.1 (s, CO$_2$), 170.9-172.2 (C4+C6, not resolved). MW calcd. for C$_{23}$H$_{15}$N$_5$O$_4$: 425.40 g/mol.

Example 35

Preparation of 3-{[4-(3-nitrophenoxy)-6-phenoxy-1,3,5-triazin-2-yl]amino}benzoic acid (35)

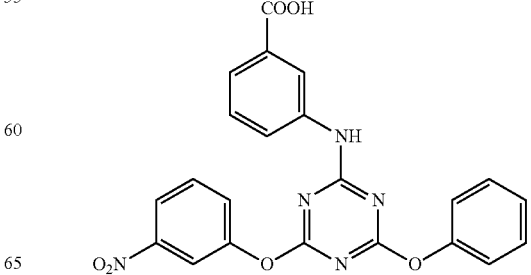

(35)

Preparation was performed according to the above general procedure C from 3-{[4-(3-nitrophenoxy)-6-phenoxy-1,3,5-triazin-2-yl]amino}benzoic acid t-butyl ester (28) (40 mg, 0.08 mmol) obtained in example 25 at 45° C. for 1 hr, which gave a beige solid (36 mg, quantitative). Mp.: 225-228° C. (Et$_2$O), RH: 0.51 (hexane:EtOH=1:1), $^1$H-NMR (DMSO-d$_6$, 200 MHz): δ=7.16-7.33 (m, 4H), 7.34-7.50 (m, 2H), 7.57 (d, J$_3$=7.7 Hz, 1H), 7.63-7.84 (m, 3H), 8.06 (s, 1H, H2'), 8.15 (d, J$_3$=7.5 Hz, 1H), 8.22 (m, 1H, H2"), 10.49 (s, 1H, NH), 12.83 (bs, 1H, CO$_2$H), $^{13}$C-NMR (DMSO-d$_6$, 50 MHz): δ=117.5 (d, C2"), 120.7 (d, C4"), 121.5 (d, C2'), 121.8 (d, C2'''+C6'''), 124.4 (d, C4'), 124.8 ((d, C6'), 125.8 (d, C4'''), 128.5 (d, C6"*), 128.9 (d, C5'*), 129.6 (d, C3'''+C5'''), 130.8 (d, C5"), 131.3 (s, C3'), 138.5 (s, C1'), 148.4 (s, C3"), 151.8 (s, C1"*), 152.0 (s, C1'''*), 166.2 (s, C2), 167.1 (s, CO$_2$), 171.2-172.5 (C4+C6, not resolved). MW calcd. for C$_{22}$H$_{15}$N$_5$O$_6$: 445.38 g/mol.

Example 36

Preparation of 3-{[4-(4-formyl-2-methoxyphenoxy)-6-phenoxy-1,3,5-triazin-2-yl]-amino}benzoic acid (36)

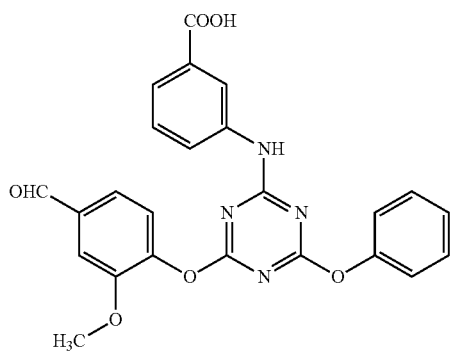 [SMILES: COc1cc(C=O)ccc1Oc1nc(Nc2cccc(C(=O)O)c2)nc(Oc2ccccc2)n1]

(36)

Preparation was performed according to the above general procedure C from 3-{[4-(4-formyl-2-methoxyphenoxy)-6-phenoxy-1,3,5-triazin-2-yl]amino}benzoic acid t-butyl ester (29) (39 mg, 0.075 mmol) obtained in example 26 at 45° C. for 1 hr, which gave a pale yellow solid (34 mg, quantitative). Mp.: 217.5-220° C. (Et$_2$O), RH: 0.62 (hexane:EtOH=1:1), $^1$H-NMR (DMSO-d$_6$, 200 MHz): δ=3.86 (s, 3H, OCH$_3$), 7.12-7.33 (m, 4H), 7.35-7.75 (m, 7H), 8.00 (s, 1H, H2'), 10.00 (s, 1H, CHO), 10.44 (s, 1H, NH); CO$_2$H not visible, $^{13}$C-NMR (DMSO-d$_6$, 50 MHz): δ=56.1 (q, OCH$_3$), 112.3 (d, C3"), 121.5 (d, C2'), 121.8 (d, C2'''+C6'''), 123.7 (d, C5"*), 123.8 (d, C4'*), 124.3 (d, C6"*), 124.7 (d, C6'), 125.8 (d, C4'''), 128.5 (d, C5'), 129.7 (d, C3'''+C5'''), 131.4 (s, C3'), 135.1 (s, C4"), 138.5 (s, C1'), 145.3 (s, C1"*), 151.70 (s, C2"*), 151.75 (s, C1'''*), 166.1 (s, C2), 167.1 (s, CO$_2$*), 171.2-172.7 (C4+C6, not resolved), 192.1 (d, CHO). MW calcd. for C$_{24}$H$_{18}$N$_4$O$_6$: 458.42 g/mol.

Example 37

Preparation of 3-{[4-(4-formyl-2-methoxyphenoxy)-6-(4-methoxyphenoxy)-1,3,5-triazin-2-yl]amino}benzoic acid (37)

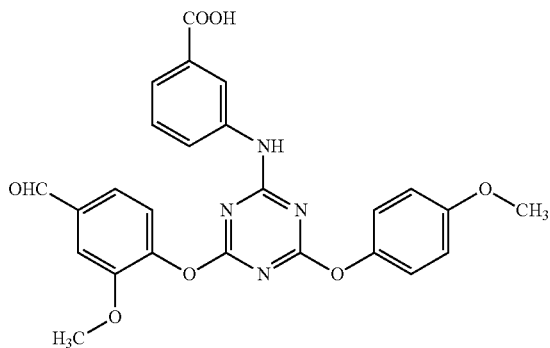

(37)

Preparation was performed according to the above general procedure C from 3-{[4-(4-formyl-2-methoxyphenoxy)-6-(4-methoxyphenoxy)-1,3,5-triazin-2-yl]amino}-benzoic acid t-butyl ester (30) (37 mg, 0.068 mmol) obtained in example 27 at 45° C. for 1.25 hrs, which gave a colorless solid (33 mg, quantitative). Mp.: 180-182° C. (Et$_2$O), RH: 0.59 (hexane:EtOH=1:1), $^1$H-NMR (DMSO-d$_6$, 200 MHz): δ=3.76 (s, 3H, C4'''OCH$_3$), 3.86 (s, 3H, C2"OCH$_3$), 6.96 (d, J$_3$=9.1 Hz, 2H, H3'''+H5'''), 7.11-7.29 (m, 3H), 7.42-7.83 (m, 5H), 8.02 (s, 1H, H2'), 10.00 (s, 1H, CHO), 10.42 (s, 1H, NH), 12.92 (bs, 1H, CO$_2$H), $^{13}$C-NMR (DMSO-d$_6$, 100 MHz): δ=55.9 (q, C4'''OCH$_3$), 56.5 (q, C2"OCH$_3$), 112.8 (d, C3"), 114.9 (d, C3'''+C5'''), 122.4 (d), 123.1 (d, C2'''+C6'''), 124.1 (d), 125.0 (d), 127.6 (d), 135.4 (s, C4"), 137.9 (s, C1'), 139.7 (s), 145.7 (s, C1"*), 145.8 (s, C1'''*), 152.2 (s, C2"), 157.3 (s, C4'''), 166.6 (s), 171.4-173.0 (C4+C6, not resolved), 192.6 (d, CHO); one s signal and two d signals were missing, probably due to overlapping. MW calcd. for C$_{25}$H$_{20}$N$_4$O$_7$: 488.45 g/mol.

Example 38

Preparation of 3-{[4-(4-cyanophenoxy)-6-(4-methoxyphenoxy)-1,3,5-triazin-2-yl]-amino}benzoic acid (38)

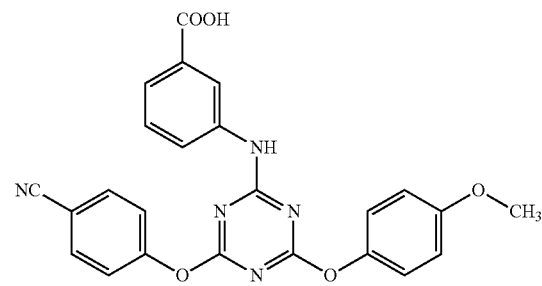 [SMILES: COc1ccc(Oc2nc(Nc3cccc(C(=O)O)c3)nc(Oc3ccc(C#N)cc3)n2)cc1]

(38)

Preparation was performed according to the above general procedure C from 3-{[4-(4-cyanophenoxy)-6-(4-methoxyphenoxy)-1,3,5-triazin-2-yl]amino}benzoic acid t-butyl ester (31) (31 mg, 0.06 mmol) obtained in example 28 at 45° C. for 1 hr, which gave a colorless solid (27 mg, quantitative). Mp.: 240.5-242.5° C. (Et$_2$O), RH: 0.48 (hexane:EtOH=1:1), $^1$H-NMR (DMSO-d$_6$, 200 MHz): δ=3.77 (s, 3H, OCH$_3$), 6.97 (d, J$_3$=9.0 Hz, 2H, H3'''+H5'''), 7.11-7.33 (m, 3H), 7.46-7.80 (m, 4H), 7.94 (d, J$_3$=8.3 Hz, 2H, H3''+H5''), 8.06 (s, 1H, H2'), 10.44 (s, 1H, NH); CO$_2$H not visible, $^{13}$C-NMR (DMSO-d$_6$, 50 MHz): δ=55.5 (q, OCH$_3$), 108.6 (s, C4''), 114.5 (d, C3'''+C5'''), 118.5 (s, CN), 121.7 (d, C2'), 122.6 (d, C2'''+C6'''), 123.3 (d, C2''+C6''), 124.4 (d, C4'), 124.9 (d, C6'), 128.6 (d, C5'), 131.4 (s, C3'), 134.2 (d, C3''+C5''), 138.5 (s, C1'), 145.2 (s, C1''), 155.2 (s, C1'''), 156.9 (s, C4'''), 166.2 (s, C2), 167.1 (s, CO$_2$); C4+C6 not visible. MW calcd. for C$_{24}$H$_{17}$N$_5$O$_5$: 455.42 g/mol.

Example 39

Preparation of {4-[(4,6-diphenoxy-1,3,5-triazin-2-yl)amino]phenyl}methanol (39)

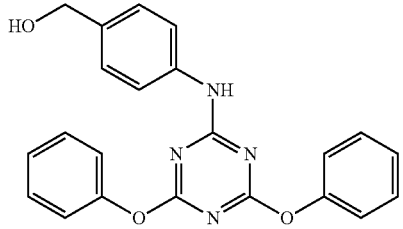 [SMILES: OCc1ccc(Nc2nc(Oc3ccccc3)nc(Oc3ccccc3)n2)cc1]
(39)

Preparation was performed according to the above general procedure D from 4-[(4,6-diphenoxy-1,3,5-triazin-2-yl)amino]benzoic acid ethyl ester (8) (32 mg, 0.075 mmol) obtained in example 5 with DIBAL-H (0.33 ml, 0.285 mmol) for 2.25 hrs and more DIBAL-H (0.05 ml, 0.045 mmol) for 1 hr. After workup according to the general procedure, the compound was dried in vacuo and did not require further purification. It was recovered as a colorless powder (29 mg, quantitative). Mp.: 152.5-154° C. (CH$_2$Cl$_2$), RH: 0.36 (hexane:EtOAc=1:1), $^1$H-NMR (DMSO-d$_6$, 200 MHz): δ=4.37 (d, J$_3$=5.6 Hz, 2H, CH$_2$), 5.07 (t, J$_3$=5.6 Hz, 1H, OH), 7.04 (d, J$_3$=8.5 Hz, 2H, H3'+H5'), 7.21-7.54 (m, 12H), 10.20 (s, 1H, NH), $^{13}$C-NMR (DMSO-d$_6$, 50 MHz): δ=62.5 (t, OCH$_2$), 120.0 (d, C2'+C6'), 121.9 (d, C2''+C2'''+C6''+C6'''), 125.7 (d, C4''+C4'''), 126.6 (d, C3'+C5'), 129.6 (d, C3''+C3'''+C5''+C5'''), 137.0 (s, C4'*), 137.4 (s, C1'*), 151.9 (s, C1''+C1'''), 165.8 (s, C2), 171.7+172.4 (s, C4+C6, rotamers). MW calcd. for C$_{22}$H$_{18}$N$_4$O$_3$: 386.40 g/mol.

Example 40

Preparation of {3-[(4,6-diphenoxy-1,3,5-triazin-2-yl)amino]phenyl}methanol (40)

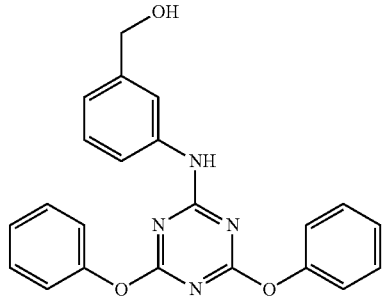 [SMILES: OCc1cccc(Nc2nc(Oc3ccccc3)nc(Oc3ccccc3)n2)c1]
(40)

Preparation was performed according to the above general procedure D from 3-[(4,6-diphenoxy-1,3,5-triazin-2-yl)amino]benzoic acid ethyl ester (9) (31 mg, 0.075 mmol) obtained in example 6 with DIBAL-H (0.33 ml, 0.285 mmol) for 1 hr. After workup according to the general procedure, the compound was dried in vacuo and did not require further purification. It was recovered as a colorless powder (29 mg, quantitative). Mp.: 49-52° C. (CH$_2$Cl$_2$), RH: 0.36 (hexane:EtOAc=1:1), $^1$H-NMR (DMSO-d$_6$, 200 MHz): δ=4.27 (d, J$_3$=5.7 Hz, 2H, OCH$_2$), 5.09 (t, J$_3$=5.7 Hz, 1H, OH), 6.95 (d, J$_3$=7.3 Hz, 1H), 7.07 (t, J$_3$=7.7 Hz, 1H, H5'), 7.20-7.38 (m, 8H), 7.39-7.53 (m, 4H), 10.22 (s, 1H, NH), $^{13}$C-NMR (DMSO-d$_6$, 50 MHz): δ=62.8 (t, CH$_2$), 118.3 (d, C2'*), 118.8 (d, C6'*), 121.3 (d, C4'*), 121.8 (d, C2''+C2'''+C6''+C6'''), 125.6 (d, C4''+C4'''), 127.9 (d, C5'), 129.5 (d, C3''+C3'''+C5''+C5'''), 138.0 (s, C1'), 142.9 (s, C3'), 151.9 (s, C1''+C1'''), 166.0 (s, C2); C4+C6 not visible. MW calcd. for C$_{22}$H$_{18}$N$_4$O$_3$: 386.40 g/mol.

Example 41

Preparation of {3-[(4-(4-chlorophenoxy)-6-phenoxy-1,3,5-triazin-2-yl)amino]phenyl}-methanol (41)

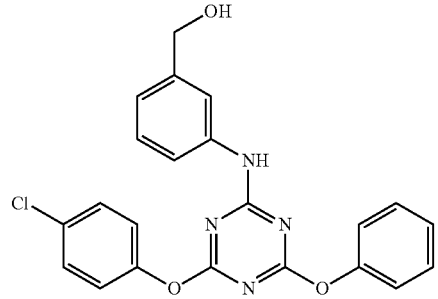 [SMILES: OCc1cccc(Nc2nc(Oc3ccccc3)nc(Oc3ccc(Cl)cc3)n2)c1]
(41)

Preparation was performed according to the above general procedure D from 3-{[4-(4-chlorophenoxy)-6-phenoxy-1,3,5-triazin-2-yl]amino}benzoic acid methyl ester (10) (34 mg, 0.075 mmol) obtained in example 7 with DIBAL-H (0.35 ml, 0.30 mmol) for 2.25 hrs and more DIBAL-H (0.05 ml, 0.045 mmol) for 1 hr. After workup according to the general procedure, the compound was recrystallized from CHCl$_3$ (1.5 ml) and n-hexane (10 ml) and dried in vacuo. A colorless solid was obtained (28 mg, 89% of theory). Mp.: 110.5-114° C. (CH$_2$Cl$_2$/hexane), RH: 0.39 (hexane:EtOAc=1:1), $^1$H-NMR (DMSO-d$_6$, 200 MHz): δ=4.24-4.34 (m 2H, OCH$_2$), 5.06-5.16 (m, 1H, OH), 6.97 (d, J$_3$=7.0 Hz, 1H), 7.09 (t, J$_3$=7.6 Hz, 1H, H5'), 7.20-7.39 (m, 7H), 7.39-7.57 (m, 4H), 10.24 (s, 1H, NH), $^{13}$C-NMR (DMSO-d$_6$, 50 MHz): δ=62.8 (t, CH$_2$), 118.4 (d, C2'*), 118.9 (d, C6'*), 121.4 (d, C4'*), 121.8 (d, C2'''+C6'''), 123.9 (d, C2''+C6''), 125.7 (d, C4'''), 128.0 (d, C5'), 129.5 (d, C3'''*+C5'''*), 129.6 (d, C3''*+C5''*), 129.9 (s, C4''), 138.0 (s, C1'), 143.0 (s, C3'), 150.7 (s, C1''), 151.8 (s, C1'''), 165.9 (s, C2); C4+C6 not visible. MW calcd. for C$_{22}$H$_{17}$ClN$_4$O$_3$: 420.85 g/mol.

Example 42

Preparation of {3-[(4-(3-chlorophenoxy)-6-phenoxy-1,3,5-triazin-2-yl)amino]phenyl}-methanol (42)

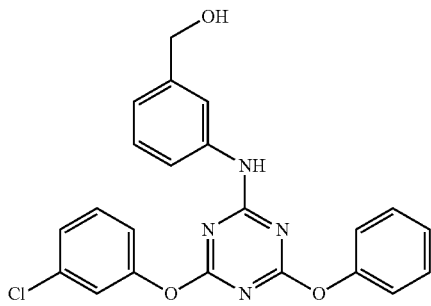 [SMILES: OCc1cccc(Nc2nc(Oc3ccccc3)nc(Oc3cccc(Cl)c3)n2)c1]

Preparation was performed according to the above general procedure D from 3-{[4-(3-chlorophenoxy)-6-phenoxy-1,3,5-triazin-2-yl]amino}benzoic acid methyl ester (11) (34 mg, 0.075 mmol) obtained in example 8 with DIBAL-H (0.45 ml, 0.385 mmol) for 1.75 hrs. After workup according to the general procedure, the crude product was purified by column chromatography (MPLC, silica gel, flow rate: 8 ml/min, PE:EtOAc=1:1) and dried in vacuo. A colorless oil was obtained (25 mg, 78% of theory). RH: 0.49 (hexane:EtOAc=1:1), $^1$H-NMR (DMSO-$d_6$, 200 MHz): $\delta$=4.30 (d, $J_3$=4.6 Hz, 2H, OCH$_2$), 5.11 (t, $J_3$=5.4 Hz, 1H, OH), 6.97 (d, $J_3$=7.5 Hz, 1H), 7.10 (t, $J_3$=7.7 Hz, 1H, H5'), 7.20-7.41 (m, 7H), 7.41-7.55 (m, 4H), 10.27 (s, 1H, NH), $^{13}$C-NMR (DMSO-$d_6$, 50 MHz): $\delta$=62.7 (t, CH$_2$), 118.4 (d, C2'*), 118.9 (d, C6'*), 120.8 (d, C6"), 121.4 (d, C4'*), 121.7 (d, C2'''+C6'''), 122.3 (d, C2"), 125.6 (d, C4"*), 125.8 (d, C4"*), 128.0 (d, C5'), 129.5 (d, C3'''+C5'''), 130.9 (d, C5"), 133.3 (s, C3"), 138.0 (s, C1'), 142.9 (s, C3'), 151.8 (s, C1'''), 152.5 (s, C1"), 165.9 (s, C2); C4+C6 not visible. MW calcd. for C$_{22}$H$_{17}$ClN$_4$O$_3$: 420.85 g/mol.

Example 43

Preparation of {3-[(4-(2-chlorophenoxy)-6-phenoxy-1,3,5-triazin-2-yl)amino]phenyl}-methanol (43)

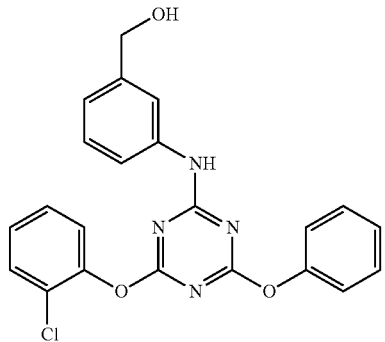 [SMILES: OCc1cccc(Nc2nc(Oc3ccccc3)nc(Oc3ccccc3Cl)n2)c1]

Preparation was performed according to the above general procedure D from 3-{[4-(2-chlorophenoxy)-6-phenoxy-1,3,5-triazin-2-yl]amino}benzoic acid methyl ester (12) (34 mg, 0.075 mmol) obtained in example 9 with DIBAL-H (0.35 ml, 0.30 mmol) for 2 hrs and more DIBAL-H (0.10 ml, 0.085 mmol) for 1.75 hrs. After workup according to the general procedure, the crude product was purified by column chromatography (MPLC, silica gel, flow rate: 15 ml/min, PE:EtOAc=3:5) and dried in vacuo. A colorless solid was obtained (32 mg, quantitative). Mp.: 52-54° C. (PE/EtOAc), RH: 0.44 (hexane:EtOAc=1:1), $^1$H-NMR (DMSO-$d_6$, 200 MHz): $\delta$=4.27 (d, $J_3$=5.3 Hz, 2H, OCH$_2$), 5.09 (t, $J_3$=5.6 Hz, 1H, OH), 6.92-7.12 (m, 2H), 7.17-7.53 (m, 10H), 7.63 (d, $J_3$=7.4 Hz, 1H), 10.31 (s, 1H, NH), $^{13}$C-NMR (DMSO-$d_6$, 50 MHz): $\delta$=62.8 (t, CH$_2$), 118.3 (d, C2'*), 118.8 (d, C6'*), 121.4 (d, C4'*), 121.8 (d, C2'''+C6'''), 124.1 (d, C6"), 125.7 (d, C4'''), 125.9 (s, C2"), 127.4 (d, C4"), 127.9 (d, C5'), 128.5 (d, C5"), 129.5 (d, C3'''+C5'''), 130.2 (d, C3"), 137.9 (s, C1'), 142.9 (s, C3'), 147.8 (s, C1"), 151.7 (s, C1'''), 165.8 (s, C2); C4+C6 not visible. MW calcd. for C$_{22}$H$_{17}$ClN$_4$O$_3$: 420.85 g/mol.

Example 44

Preparation of {3-[(4-(4-t-butylphenoxy)-6-phenoxy-1,3,5-triazin-2-yl)amino]phenyl}-methanol (44)

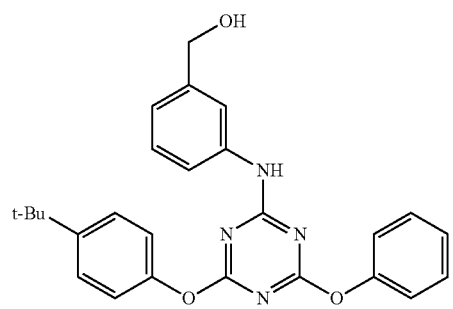 [SMILES: CC(C)(C)c1ccc(Oc2nc(Nc3cccc(CO)c3)nc(Oc3ccccc3)n2)cc1]

Preparation was performed according to the above general procedure D from 3-{[4-(4-t-butylphenoxy)-6-phenoxy-1,3,5-triazin-2-yl]amino}benzoic acid methyl ester (13) (35 mg, 0.075 mmol) obtained in example 10 with DIBAL-H (0.45 ml, 0.385 mmol) for 1.5 hrs. After workup according to the general procedure, the compound was dried in vacuo, and no further purification was required. A colorless solid was obtained (33 mg, quantitative). Mp.: 47-50° C. (CH$_2$Cl$_2$/hexane), RH: 0.54 (hexane:EtOAc=1:1), $^1$H-NMR (DMSO-$d_6$, 200 MHz): $\delta$=1.31 (s, 9H, (CH$_3$)$_3$), 4.28 (d, $J_3$=4.5 Hz, 2H, OCH$_2$), 5.11 (bs, 1H, OH), 6.95 (d, $J_3$=7.5 Hz, 1H), 7.06 (t, $J_3$=7.7 Hz, 1H, H5'), 7.12-7.21 (m, 2H), 7.22-7.34 (m, 4H), 7.35-7.52 (m, 5H), 10.20 (s, 1H, NH), $^{13}$C-NMR (DMSO-$d_6$, 50 MHz): $\delta$=31.2 (q, C(CH$_3$)$_3$), 34.2 (s, C(CH$_3$)$_3$), 62.8 (t, CH$_2$), 118.3 (d, C2'*), 118.8 (d, C6'*), 121.1 (d, C2'"*+C6'"*), 121.3 (d, C4'*), 121.8 (d, C2'''+C6'''), 125.6 (d, C4'''), 126.2 (d, C3"+C5"), 127.9 (d, C5'), 129.5 (d, C3'''+C5'''), 138.1 (s, C1'), 142.9 (s, C3'), 147.9 (s, C4"*), 149.5 (s, C1"*), 151.8 (s, C1'''), 165.9 (s, C2); C4+C6 not visible. MW calcd. for C$_{26}$H$_{26}$N$_4$O$_3$: 442.51 g/mol.

Example 45

Preparation of {3-[(4-(4-methoxyphenoxy)-6-phenoxy-1,3,5-triazin-2-yl)amino]-phenyl}methanol (45)

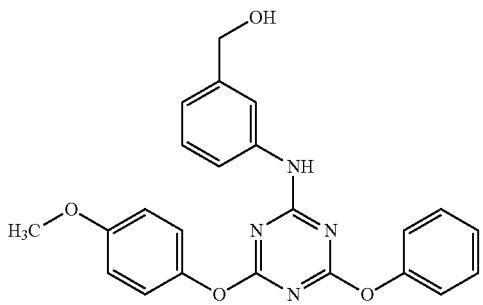 [SMILES: COc1ccc(Oc2nc(Nc3cccc(CO)c3)nc(Oc3ccccc3)n2)cc1]

(45)

Preparation was performed according to the above general procedure D from 3-{[4-(4-methoxyphenoxy)-6-phenoxy-1,3,5-triazin-2-yl]amino}benzoic acid methyl ester (14) (33 mg, 0.075 mmol) obtained in example 11 with DIBAL-H (0.45 ml, 0.385 mmol) for 1.75 hrs. After workup according to the general procedure, the compound was dried in vacuo, and no further purification was required. A colorless oil was obtained (31 mg, quantitative). RH: 0.32 (hexane:EtOAc=1:1), $^1$H-NMR (DMSO-$d_6$, 200 MHz): δ=3.78 (s, 3H, OCH$_3$), 4.28 (d, $J_3$=5.7 Hz, 2H, CH$_2$), 5.10 (t, $J_3$=5.7 Hz, 1H, OH), 6.91-7-52 (m, 13H), 10.18 (s, 1H, NH), $^{13}$C-NMR (DMSO-$d_6$, 50 MHz): δ=55.4 (q, OCH$_3$), 62.8 (t, CH$_2$), 114.4 (d, C3"+C5"), 118.3 (d, C2'*), 118.8 (d, C6'*), 121.2 (d, C4'*), 121.8 (d, C2'''+C6'''), 122.6 (d, C2"+C6"), 125.6 (d, C4'''), 127.9 (d, C5'), 129.5 (d, C3'''+C5'''), 138.1 (s, C1'), 142.9 (s, C3'), 145.2 (s, C1"), 151.8 (s, C1'''), 156.8 (s, C4"), 165.9 (s, C2); C4+C6 not visible. MW calcd. for $C_{23}H_{20}N_4O_4$: 416.43 g/mol.

Example 46

Activity Tests

ANF Test

Atrial natriuretic factor (ANF) or atrial natriuretic peptide (ANP) is a cyclic peptide hormone made up of 28 amino acids, which is predominantly emitted by the muscle cells (myocytes) of the atrium of the heart. It is stored in the atrium as a pro-hormone made of 126 amino acids and is cleaved by serine protease corine into an N-terminal part and the biologically active ANF, which is often used as a cardiac-specific marker protein. In cell differentiation measurements, i.e. in determining the extent to which certain cells have become "cardiac cell-like" by differentiation, often a reporter gene located downstream of the ANF gene is used, as it expression product is easier to detect than the concentration of ANF in a cellular culture, for example, a luciferase gene. Luciferase in an enzyme which catalyzes the oxidation of a luminescent substrate (luciferine). While that happens, light is emitted, and the intensity of that light is correlated with the expression level of ANF and can therefore serve as a measure of ANF expression.

Initial attempts of ANF expression screenings were performed with P19 cells, i.e. murine embryonal carcinoma cells obtained from the ATCC, or C2C12 cells, i.e. a murine myoblast cell line, as models. In preparation, a plasmid was first constructed by amplifying a gene fragment containing a rat ANF promoter region and subcloning it into the PCL3-BV luciferase reporter plasmid of Promega. The P19 cells were temporarily transfected with said plasmid and cultured in Modified Eagle's Medium alpha (MEM-α) with 7.5% neonatal calf serum and 2.5% fetal bovine serum at 37° C. under 5% $CO_2$ in monolayers for 8 days, during which the medium was exchanged three times. The respective compounds were added at about 60% confluence in DMSO as solvents at a concentration of 1 μM or DMSO alone (as a blank). The luminescence of the samples was measured with a Perkin Elmer Victor V 1420 Multilabel Counter. Their increase or decrease in the presence of the compounds of formula (I) is given in Table 1 below in relation to the blank.

The evaluations have the following meanings:
− decrease of luminescence compared to the blank value;
+ measurable increase;
++ at least 1.5-fold increase;
+++ at least 2-fold increase;
\* represents C2C12 cells; and
\*\* represents P19 cells.

TABLE 1

| Compound # | ANF test Structure | Evaluation |
|---|---|---|
| DMSO | (structure of DMSO) | −\*<br>−\*\* |
| DTAB | (structure of DTAB) | −\*<br>−\*\* |

TABLE 1-continued

| | ANF test | |
|---|---|---|
| Compound # | Structure | Evaluation |
| (1) | 4-methoxyphenyl-NH-triazine(Cl)-NH-CH2CH2OH | +* |
| (2) | 4-methoxyphenyl-NH-triazine(Cl)-NH-CH2CH2CH2OH | ++* |
| (3) | 4-methoxyphenyl-NH-triazine(Cl)-NH-CH2CH3 | −** |
| (4) | 4-methoxyphenyl-NH-triazine-NH-CH2CH2OH | −** |
| (5) | 4-(EtOOC)phenyl-NH-triazine(OPh)(OPh) | −** |
| (7) | 3-(COOMe)phenyl-NH-triazine(O-4-chlorophenyl)(OPh) | −** |
| (8) | 3-(COOMe)phenyl-NH-triazine(O-3-chlorophenyl)(OPh) | ++** |

TABLE 1-continued

| Compound # | Structure | ANF test Evaluation |
|---|---|---|
| (9) | 3-(COOMe)C₆H₄-NH-[triazine(OPh)(O-2-ClC₆H₄)] | —** |
| (10) | 3-(COOMe)C₆H₄-NH-[triazine(OPh)(O-4-tBuC₆H₄)] | —** |
| (11) | 3-(COOMe)C₆H₄-NH-[triazine(OPh)(O-4-MeOC₆H₄)] | —** |
| (12) | 3-(COOMe)C₆H₄-NH-[triazine(OPh)(O-4-NCC₆H₄)] | —** |
| (13) | 3-(COOMe)C₆H₄-NH-[triazine(OPh)(O-3-O₂NC₆H₄)] | —** |

TABLE 1-continued

| Compound # | Structure | Evaluation |
|---|---|---|
| (29) | 3-(4-((4-chlorophenoxy)-6-phenoxy-1,3,5-triazin-2-ylamino)benzoic acid | +++** |
| (30) | 3-(4-((3-chlorophenoxy)-6-phenoxy-1,3,5-triazin-2-ylamino)benzoic acid | ++** |
| (31) | 3-(4-((2-chlorophenoxy)-6-phenoxy-1,3,5-triazin-2-ylamino)benzoic acid | ++** |
| (32) | 3-(4-((4-tert-butylphenoxy)-6-phenoxy-1,3,5-triazin-2-ylamino)benzoic acid | +** |
| (33) | 3-(4-((4-methoxyphenoxy)-6-phenoxy-1,3,5-triazin-2-ylamino)benzoic acid | +** |

TABLE 1-continued

| | ANF test | |
|---|---|---|
| Compound # | Structure | Evaluation |
| (34) | 3-[[4-(4-cyanophenoxy)-6-phenoxy-1,3,5-triazin-2-yl]amino]benzoic acid | +** |
| (35) | 3-[[4-(3-nitrophenoxy)-6-phenoxy-1,3,5-triazin-2-yl]amino]benzoic acid | ++** |
| (36) | 3-[[4-(4-formyl-2-methoxyphenoxy)-6-phenoxy-1,3,5-triazin-2-yl]amino]benzoic acid | +++** |
| (38) | 3-[[4-(4-cyanophenoxy)-6-(4-methoxyphenoxy)-1,3,5-triazin-2-yl]amino]benzoic acid | ++** |
| (39) | 4-[(4,6-diphenoxy-1,3,5-triazin-2-yl)amino]phenylmethanol | +++** |

TABLE 1-continued
| Compound # | Structure | Evaluation |
|---|---|---|
| (40) | 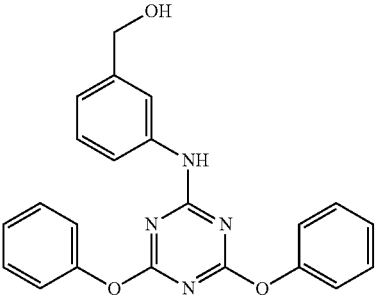 | +** |
| (41) | 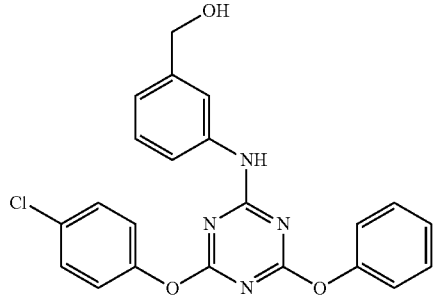 | −** |
| (42) | 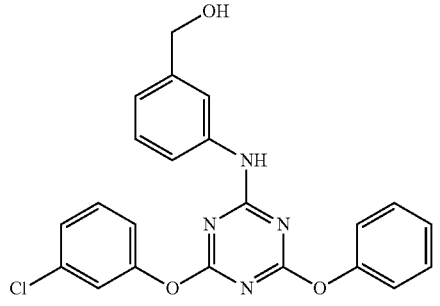 | +** |
| (43) | 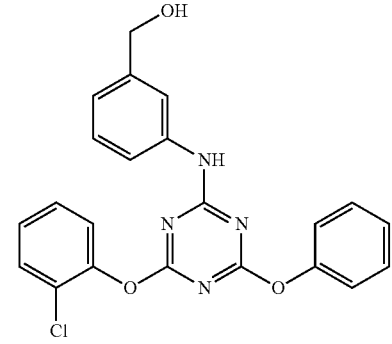 | −** |
| (44) | 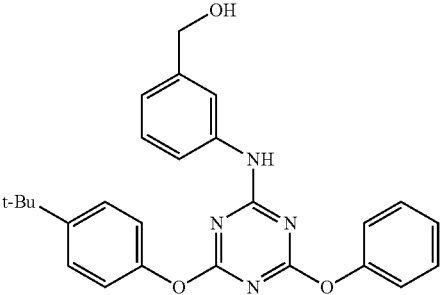 | +++** |

TABLE 1-continued

ANF test

| Compound # | Structure | Evaluation |
|---|---|---|
| (45) | (structure shown) | +** |

For DTAB, which served as a reference substance, substantially no changes in the ANF expression level were found, even a slight decrease. On the other hand, a few of the compounds of formula (I) caused strong increases of luminescence and the amounts of ANF, while others produced even worse results than DTAB. From the above table, however, it is difficult to deduce clear connections between the structure of the compounds and their effectiveness as differentiation catalysts.

Out of the 4 amino-anilino compounds (1) to (4) that were tested, compound (2) showed very good efficiency, while (3) and (4) produced the poorest measurement results among all compounds.

Out of the 24 anilino-diphenoxy compounds, i.e. derivatives of DTAB, 9 (i.e. about one third) showed an even more disadvantageous effect than DTAB, while 15 (i.e. about two thirds) surprisingly caused a partly dramatically increased ANF expression (peak value: more than threefold for compound (36)). What was surprising on top of that, was that of all the compounds, the carboxylic acids (as DTAB itself is one) tended to show a more beneficial effect than alcohols, which themselves exhibited better results than carboxylic acid esters.

A comparison between the two groups of three chlorophenoxy derivatives each, (29) to (31) and (41) to (43), is also revealing, as they differed only by the position of the chloro substituent in one of the phenoxy residues, i.e. are p-, m- and o-derivatives, respectively (benzoic acids and benzyl alcohols, respectively). The respective evaluations are as follows:

| (29) (p-chloro): +++ | (30) (m-chloro): + | (31) (o-chloro): ++ |
| (41) (p-chloro): − | (42) (m-chloro): + | (43) (o-chloro): − |

In addition to the fact mentioned above that carboxylic acids tend to show better efficiency than alcohols, it can be seen that, in the first case, the p-chloro derivative gave the best results, while it was the m-chloro derivative in the second case. In the first case, the m-chloro derivative exhibited even the worst result among the three compounds.

Obviously, it is not only the type but also the position of the substituent that plays a substantial role, so that is hardly possible to estimate whether a certain derivative will exhibit a desired effect or not. Possibly, other conclusive statements can be made if the other compounds of formula (I) prepared herein as well as even additional compounds of formula (I) will be tested for effectiveness, which is the subject of the inventors' current research.

However, what is clear beyond doubt from the above table is that the majority (about two thirds) of the test compounds had positive effects on the expression of ANF and therefore on the differentiation of the cells, which was indeed surprising considering the effect of DTAB known from the literature, and which forms the basis for the present invention.

The invention claimed is:

1. A method of inducing differentiation of a mammalian pluripotent stem cell or myoblast cell into a cardiomyocyte-like cell, the method comprising:
   incubating the mammalian cell with at least one compound of formula (I)

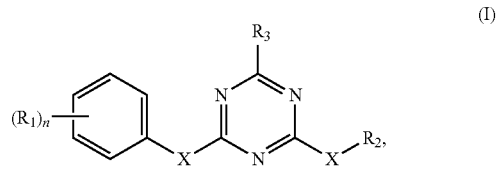

in an amount effective to induce the differentiation, wherein:
   X is independently —$NR_4$— or —O—, the $R_4$ being hydrogen or $C_{1-6}$-alkyl;
   $R_1$ is hydroxy, $C_{1-6}$-alkyl, $C_{1-6}$-alkoxy, carboxy, $C_{1-6}$-alkoxycarbonyl, halo, cyano, nitro, formyl, amino, $C_{1-6}$-alkylamino, or di-$C_{1-6}$-alkylamino, the $C_{1-6}$-alkyl or -alkoxy being optionally substituted with one or more $R_5$, the $R_5$ being hydroxy, halo, cyano, or nitro;
   n is 0 to 5;
   $R_2$ is hydrogen, aryl, heteroaryl, or $C_{1-6}$-alkyl, the aryl or heteroaryl optionally substituted with one or more $R_6$, identical options applying for $R_6$ as for $R_1$ and the $C_{1-6}$-alkyl optionally further substituted by one or more $R_5$; and
   $R_3$ is hydrogen, halo, $NR_4R_7$, $OR_7$, $SR_S$, and $R_7$, identical options applying for $R_7$ as for $R_2$,
   with the proviso that the compound of formula (I) is not 3-[(4,6-diphenoxy-1,3,5-triazin-2-yl)amino]benzoic acid.

2. The method of claim 1, wherein $R_1$ is t-butyl, meth-oxy, hydroxymethyl, carboxy, methoxycarbonyl, t-butoxycarbonyl, cyano, formyl, nitro, or chloro.

3. The method of claim 1, wherein $R_2$ is selected from phenyl, ethyl, and propyl.

4. The method of claim 1, wherein $R_3$ is hydrogen, chloro, —$NR_4R_7$, or $R_7$.

5. The method of claim 1, wherein $R_4$ is hydrogen.

6. The method of claim 1, wherein $R_5$ is hydroxy.

7. The method of claim 1, wherein $R_6$ is t-butyl, methoxy, hydroxymethyl, carboxy, methoxycarbonyl, t-butoxycarbonyl, cyano, formyl, nitro, or chloro.

8. The method of claim 1, wherein $R_7$ is phenyl optionally substituted with one or two $R_6$.

9. The method of claim 1, wherein both X are either —O— or —NH—.

10. The method of claim 9, wherein both X are —O—, and
wherein $R_3$ is $NHR_7$.

11. The method of claim 10, wherein the compound of formula (I) is an anilinodiphenoxytriazine of formula (II),

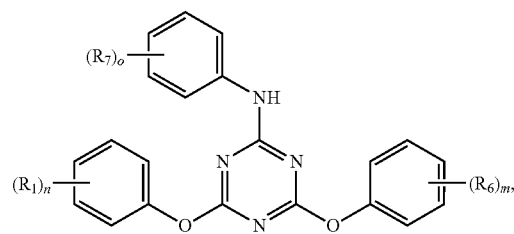

wherein n, m, and o are independently 0 to 5.

12. The method of claim 9, wherein both X are —NH—, and
wherein $R_3$ is hydrogen or chloro.

13. The method of claim 1, wherein n is 0, 1, or 2.

14. The method of claim 1, wherein the compound of formula (I) comprises:
2-[4-chloro-6-(4-methoxyphenylamino)-1,3,5-triazin-2-ylamino]ethanol (1),
3-[4-chloro-6-(4-methoxyphenylamino)-1,3,5-triazin-2-ylamino]propan-1-ol (2),
3-{[4-(3-chlorophenoxy)-6-phenoxy-1,3,5-triazin-2-yl]amino}benzoic acid methyl ester (8),
3-{[4-(4-chlorophenoxy)-6-phenoxy-1,3,5-triazin-2-yl]amino}benzoic acid (29),
3-{[4-(3-chlorophenoxy)-6-phenoxy-1,3,5-triazin-2-yl]amino}benzoic acid (30),
3-{[4-(2-chlorophenoxy)-6-phenoxy-1,3,5-triazin-2-yl]amino}benzoic acid (31),
3-{[4-(4-t-butylphenoxy)-6-phenoxy-1,3,5-triazin-2-yl]amino}benzoic acid (32),
3-{[4-(4-methoxyphenoxy)-6-phenoxy-1,3,5-triazin-2-yl]amino}benzoic acid (33),
3-{[4-(4-cyanophenoxy)-6-phenoxy-1,3,5-triazin-2-yl]amino}benzoic acid (34),
3-{[4-(3-nitrophenoxy)-6-phenoxy-1,3,5-triazin-2-yl]amino}benzoic acid (35),
3-{[4-(4-formyl-2-methoxyphenoxy)-6-phenoxy-1,3,5-triazin-2-yl]amino}benzoic acid (36),
3-{[4-(4-cyanophenoxy)-6-(4-methoxyphenoxy)-1,3,5-triazin-2-yl]amino}benzoic acid (38),
{4-[(4.6-diphenoxy-1,3,5-triazin-2-yl)amino]phenyl}methanol (39),
{3-[(4.6-diphenoxy-1,3,5-triazin-2-yl)amino]phenyl}methanol (40),
{3-[(4-(3-chlorophenoxy)-6-phenoxy-1,3,5-triazin-2-yl)amino]phenyl}methanol (42),
{3-[(4-(4-t-butylphenoxy)-6-phenoxy-1,3,5-triazin-2-yl)amino]phenyl}methanol (44),
{3-[(4-(4-methoxyphenoxy)-6-phenoxy-1,3,5-triazin-2-yl)amino]phenyl}methanol (45),
or a mixture of two or more thereof.

15. The method of claim 1, wherein the compound of formula (I) comprises:
3-[4-chloro-6-(4-methoxyphenylamino)-1,3,5-triazin-2-ylamino]propan-1-ol (2),
3-{[4-(3-chlorophenoxy)-6-phenoxy-1,3,5-triazin-2-yl]amino}benzoic acid methyl ester (8),
3-{[4-(4-chlorophenoxy)-6-phenoxy-1,3,5-triazin-2-yl]amino}benzoic acid (29),
3-{[4-(3-chlorophenoxy)-6-phenoxy-1,3,5-triazin-2-yl]amino}benzoic acid (30),
3-{[4-(2-chlorophenoxy)-6-phenoxy-1,3,5-triazin-2-yl]amino}benzoic acid (31),
3-{[4-(3-nitrophenoxy)-6-phenoxy-1,3,5-triazin-2-yl]amino}benzoic acid (35),
3-{[4-(4-formyl-2-methoxyphenoxy)-6-phenoxy-1,3,5-triazin-2-yl]amino}benzoic acid (36),
3-{[4-(4-cyanophenoxy)-6-(4-methoxyphenoxy)-1,3,5-triazin-2-yl]amino}benzoic acid (38),
{4-[(4.6-diphenoxy-1,3,5-triazin-2-yl)amino]phenyl}methanol (39),
{3-[(4-(4-t-butylphenoxy)-6-phenoxy-1,3,5-triazin-2-yl)amino]phenyl}methanol (44),
or a mixture of two or more thereof.

16. The method of claim 1, wherein the compound of formula (I) comprises:
3-{[4-(4-chlorophenoxy)-6-phenoxy-1,3,5-triazin-2-yl]amino}benzoic acid (29),
3-{[4-(4-formyl-2-methoxyphenoxy)-6-phenoxy-1,3,5-triazin-2-yl]amino}benzoic acid (36),
{4-[(4.6-diphenoxy-1,3,5-triazin-2-yl)amino]phenyl}methanol (39),
{3-[(4-(4-t-butylphenoxy)-6-phenoxy-1,3,5-triazin-2-yl)amino]phenyl}methanol (44),
or a mixture of two or more thereof.

17. The method of claim 11, wherein n, m, and o are independently 0, 1, or 2.

18. The method of claim 1, wherein the cardiomyocyte-like cell comprises a cell exhibiting an increased expression of atrial natriuretic factor (ANF).

19. The method of claim 1, wherein the compound of formula (I) comprises 3-{[4-(4-chlorophenoxy)-6-phenoxy-1,3,5-triazin-2-yl]amino }benzoic acid (29).

20. The method of claim 1, wherein the compound of formula (I) comprises {3-[(4-(4-t-butylphenoxy)-6-phenoxy-1,3,5-triazin-2-yl)amino]phenyl}methanol (44).

* * * * *